United States Patent
Chang et al.

(10) Patent No.: US 8,026,110 B2
(45) Date of Patent: Sep. 27, 2011

(54) COMBINATORIAL ROSAMINE LIBRARY AND USES THEREOF

(75) Inventors: Young-Tae Chang, Kent Vale (SG); Young-Hoon Ahn, New York, NY (US)

(73) Assignee: New York University, New York, NY (US)

( * ) Notice: Subject to any disclaimer, the term of this patent is extended or adjusted under 35 U.S.C. 154(b) by 1028 days.

(21) Appl. No.: 11/853,594

(22) Filed: Sep. 11, 2007

(65) Prior Publication Data
US 2008/0124751 A1 May 29, 2008

Related U.S. Application Data

(60) Provisional application No. 60/844,176, filed on Sep. 13, 2006.

(51) Int. Cl.
C12Q 1/02 (2006.01)
C40B 70/00 (2006.01)
C40B 40/06 (2006.01)

(52) U.S. Cl. .............. 436/800; 501/41; 501/15; 435/29; 436/96

(58) Field of Classification Search .................. None
See application file for complete search history.

(56) References Cited

U.S. PATENT DOCUMENTS

| 2003/0166002 A1 | 9/2003 | Chang et al. |
| 2004/0122009 A1 | 6/2004 | Chang et al. |
| 2004/0225125 A1 | 11/2004 | Chang |
| 2004/0265252 A1 | 12/2004 | Orlow et al. |
| 2005/0019831 A1 | 1/2005 | Chang |
| 2005/0054006 A1 | 3/2005 | Chang et al. |
| 2005/0227293 A1 | 10/2005 | Chang |

FOREIGN PATENT DOCUMENTS

WO  WO2005033149  4/2005

OTHER PUBLICATIONS

Muller et al (1975 Eur. J. Biochem 54: 279-291).*
Jiao et al., "Microwave-Assisted Syntheses of Regioisomerically Pure Bromorhodamine Derivatives," Organic Letters, 5:3675-3677 (2003).
Liu et al., "Rational Design and Synthesis of a Novel Class of Highly Fluorescent Rhodamine Dyes That Have Strong Absorption At Long Wavelengths," Tetrahedron Letters, 44:4355-4359 (2003).
Li et al., "Solid-Phase Synthesis of Styryl Dyes and Their Application As Amyloid Sensors," Angew Chem. Int. Ed., 43:6331-6335 (2004).

* cited by examiner

*Primary Examiner* — Christopher M Gross
(74) *Attorney, Agent, or Firm* — LeClairRyan

(57) ABSTRACT

The present invention relates to a rosamine derivative compound, as described herein, having the following structure:

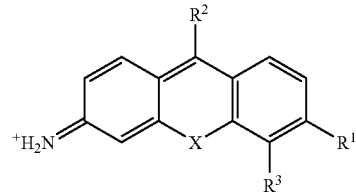

Also disclosed are methods of making such compounds and for using them for detection and imaging.

25 Claims, 20 Drawing Sheets

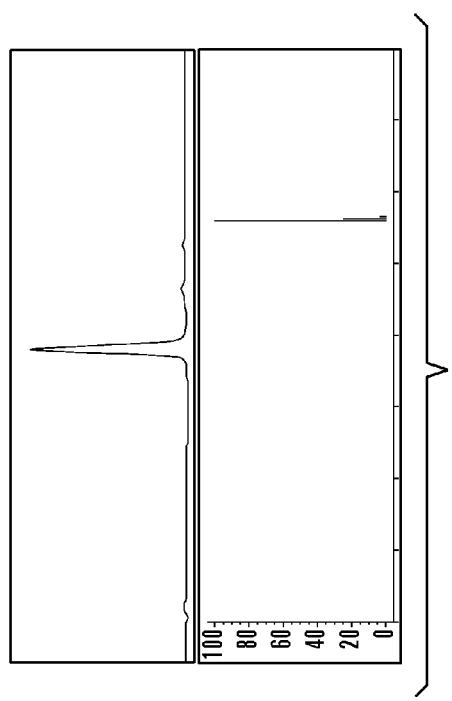
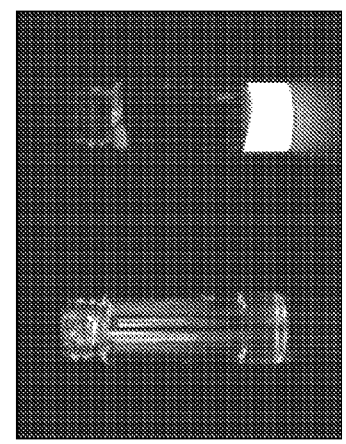
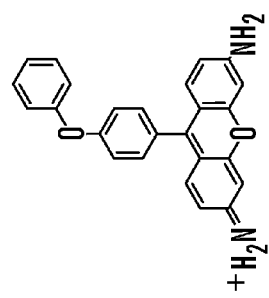
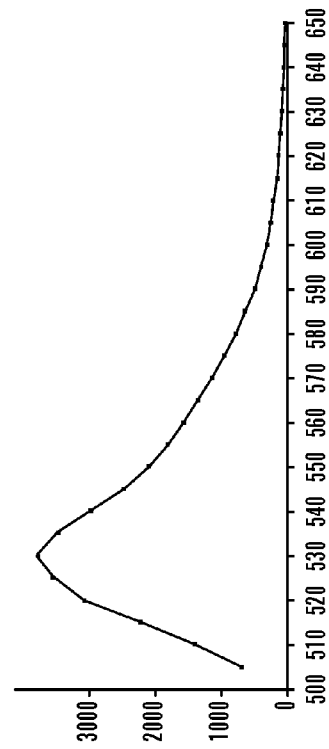
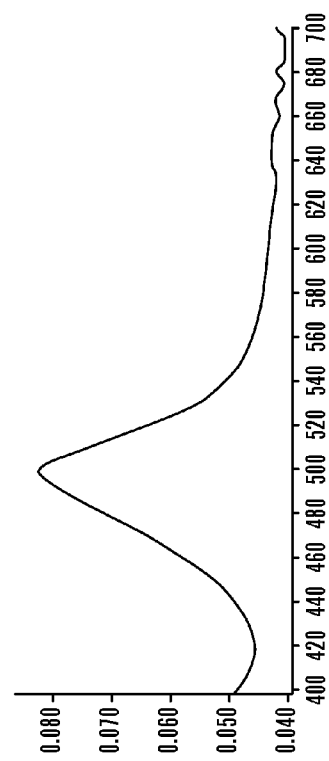
FIG. 6A
FIG. 6B
FIG. 6C
FIG. 6D

FIG. 8

| CODE | λab(nm)[a] | λem(nm)[b] | PURITY%[c] | MASS[d] (CALC.) | MASS[e] (FOUND) | CODE | λab(nm)[a] | λem(nm)[b] | PURITY%[c] | MASS[d] (CALC.) | MASS[e] (FOUND) |
|---|---|---|---|---|---|---|---|---|---|---|---|
| A-1 | 505 | 530 | 88 | 305.1 | 305.3 | F-9 | 510 | 540 | 89 | 391.2 | 391.2 |
| A-2 | 500 | 530 | 90 | 330.2 | 330.3 | F-15 | 510 | 540 | 85 | 315.2 | 315.2 |
| A-3 | 500 | 530 | 91 | 317.1 | 317.3 | F-16 | 515 | 540 | 95 | 343.2 | 343.2 |
| A-4 | 495 | 530 | 91 | 379.1 | 379.4 | F-17 | 515 | 540 | 87 | 345.2 | 345.1 |
| A-5 | 500 | 530 | 93 | 303.1 | 303.1 | F-19 | 520 | 540 | 91 | 333.1 | 333.1 |
| A-6 | 525 | 540 | 91 | 327.0 | 327.1 | F-20 | 525 | 545 | 95 | 349.1 | 349.1 |
| A-7 | 500 | 535 | 91 | 337.2 | 337.3 | F-21 | 530 | 545 | 95 | 343.1 | 343.1 |
| A-8 | 505 | 530 | 91 | 333.1 | 333.3 | F-23 | 510 | 540 | 94 | 329.2 | 329.2 |
| A-9 | 490 | 530 | 93 | 363.1 | 363.3 | F-25 | 510 | 540 | 92 | 373.2 | 373.2 |
| A-10 | 505 | 530 | 94 | 339.1 | 339.3 | F-27 | 515 | 540 | 92 | 347.2 | 347.2 |
| A-11 | 525 | 530 | 88 | 387.1 | 387.1 | G-1 | 520 | 550 | 94 | 321.1 | 321.1 |
| A-12 | 510 | 535 | 93 | 341.1 | 341.3 | G-2 | 520 | 550 | 88 | 346.1 | 346.1 |
| A-13 | 500 | 530 | 91 | 367.1 | 367.4 | G-3 | 520 | 550 | 90 | 333.1 | 333.1 |
| A-15 | 500 | 530 | 93 | 287.1 | 287.2 | G-4 | 515 | 540 | 90 | 395.1 | 395.2 |
| A-16 | 500 | 530 | 94 | 315.1 | 315.2 | G-5 | 520 | 550 | 85 | 319.1 | 319.1 |
| A-17 | 500 | 530 | 92 | 317.1 | 317.2 | G-7 | 520 | 545 | 96 | 353.1 | 353.1 |
| A-18 | 500 | 530 | 90 | 331.1 | 331.3 | G-9 | 520 | 550 | 100 | 379.1 | 379.1 |
| A-19 | 500 | 530 | 90 | 305.1 | 305.1 | G-11 | 530 | 555 | 100 | 403.1 | 403.1 |
| A-20 | 505 | 535 | 91 | 321.1 | 321.1 | G-13 | 525 | 550 | 98 | 383.1 | 383.0 |
| A-21 | 505 | 535 | 86 | 315.1 | 315.1 | G-14 | 520 | 545 | 96 | 359.2 | 359.1 |
| A-22 | 505 | 530 | 85 | 442.2 | 442.2 | G-15 | 520 | 550 | 95 | 303.1 | 303.1 |
| A-23 | 500 | 530 | 91 | 301.1 | 301.2 | G-16 | 520 | 550 | 98 | 331.1 | 331.1 |

FIG. 11

| CODE | λab(nm)[a] | λem(nm)[b] | PURITY%[c] | MASS[d] (CALC.) | MASS[e] (FOUND) | CODE | λab(nm)[a] | λem(nm)[b] | PURITY%[c] | MASS[d] (CALC.) | MASS[e] (FOUND) |
|---|---|---|---|---|---|---|---|---|---|---|---|
| A-24 | 500 | 530 | 98 | 347.1 | 347.1 | G-17 | 520 | 550 | 98 | 333.1 | 333.1 |
| A-25 | 500 | 530 | 92 | 345.2 | 345.2 | G-18 | 525 | 550 | 90 | 347.1 | 347.1 |
| A-26 | 505 | 530 | 90 | 335.1 | 335.1 | G-19 | 525 | 555 | 96 | 321.1 | 321.1 |
| A-27 | 500 | 530 | 90 | 319.1 | 319.1 | G-20 | 525 | 555 | 96 | 337.1 | 337.1 |
| A-29 | 500 | 530 | 94 | 329.2 | 329.2 | G-21 | 525 | 555 | 100 | 331.1 | 331.1 |
| B-1 | 530 | 565 | 97 | 333.1 | 333.1 | G-22 | 525 | 550 | 90 | 458.2 | 458.1 |
| B-2 | 525 | 565 | 94 | 358.2 | 358.2 | G-23 | 520 | 550 | 99 | 317.1 | 317.1 |
| B-3 | 525 | 565 | 92 | 345.2 | 345.2 | G-25 | 520 | 550 | 98 | 361.1 | 361.1 |
| B-4 | 525 | 570 | 90 | 407.2 | 407.1 | G-27 | 520 | 550 | 99 | 335.1 | 335.1 |
| B-7 | 525 | 570 | 93 | 365.2 | 365.1 | G-29 | 520 | 550 | 100 | 345.1 | 345.1 |
| B-8 | 525 | 570 | 93 | 361.1 | 361.1 | H-1 | 540 | 570 | 91 | 385.2 | 385.1 |
| B-9 | 505 | 570 | 91 | 391.2 | 391.2 | H-2 | 540 | 0 | 96 | 410.2 | 410.2 |
| B-10 | 530 | 570 | 92 | 367.1 | 367.1 | H-3 | 535 | 570 | 93 | 397.2 | 397.1 |
| B-11 | 545 | 565 | 89 | 415.2 | 415.1 | H-4 | 540 | 565 | 93 | 459.2 | 459.1 |
| B-13 | 520 | 570 | 92 | 395.2 | 395.2 | H-7 | 540 | 570 | 87 | 417.2 | 417.2 |
| B-14 | 525 | 565 | 95 | 371.2 | 371.2 | H-8 | 535 | 570 | 90 | 413.2 | 413.1 |
| B-15 | 525 | 570 | 94 | 315.1 | 315.2 | H-9 | 540 | 570 | 91 | 443.2 | 443.1 |
| B-16 | 525 | 565 | 94 | 343.2 | 343.2 | H-15 | 540 | 565 | 91 | 367.2 | 367.2 |
| B-17 | 530 | 565 | 96 | 345.2 | 345.2 | H-16 | 540 | 565 | 94 | 395.2 | 395.2 |
| B-18 | 530 | 565 | 89 | 359.1 | 359.1 | H-17 | 540 | 565 | 91 | 397.2 | 397.2 |
| B-19 | 530 | 570 | 93 | 333.1 | 333.2 | H-18 | 535 | 575 | 89 | 411.2 | 411.1 |
| B-20 | 530 | 570 | 88 | 349.1 | 349.1 | H-19 | 540 | 565 | 94 | 385.2 | 385.2 |

*FIG. 11 (cont'd)*

| CODE | λab(nm)[a] | λem(nm)[b] | PURITY%[c] | MASS[d] (CALC.) | MASS[e] (FOUND) | CODE | λab(nm)[a] | λem(nm)[b] | PURITY%[c] | MASS[d] (CALC.) | MASS[e] (FOUND) |
|---|---|---|---|---|---|---|---|---|---|---|---|
| B-21 | 535 | 580 | 95 | 343.1 | 343.1 | H-20 | 540 | 565 | 93 | 401.1 | 401.1 |
| B-22 | 530 | 570 | 98 | 470.2 | 470.2 | H-21 | 545 | 575 | 93 | 395.2 | 395.1 |
| B-23 | 525 | 565 | 90 | 329.2 | 329.2 | H-22 | 535 | 565 | 99 | 522.3 | 522.2 |
| B-24 | 525 | 560 | 96 | 375.2 | 375.1 | H-23 | 535 | 565 | 90 | 381.2 | 381.2 |
| B-25 | 525 | 565 | 92 | 373.2 | 373.2 | H-25 | 535 | 570 | 91 | 425.2 | 425.2 |
| B-26 | 530 | 560 | 94 | 363.1 | 363.1 | H-27 | 530 | 565 | 90 | 399.2 | 399.1 |
| B-27 | 525 | 565 | 94 | 347.2 | 347.1 | H-31 | 540 | 570 | 99 | 464.3 | 464.2 |
| B-28 | 545 | 575 | 99 | 321.1 | 321.1 | H-32 | 545 | 565 | 99 | 464.3 | 464.2 |
| B-29 | 525 | 565 | 92 | 357.2 | 357.2 | I-1 | 540 | 565 | 95 | 417.2 | 417.1 |
| B-30 | 530 | 570 | 87 | 414.2 | 414.2 | I-2 | 530 | 570 | 96 | 442.3 | 442.2 |
| B-31 | 530 | 570 | 91 | 412.2 | 412.2 | I-3 | 535 | 565 | 96 | 429.3 | 429.2 |
| B-32 | 530 | 570 | 92 | 412.2 | 412.2 | I-4 | 535 | 565 | 93 | 491.3 | 491.2 |
| B-33 | 530 | 570 | 90 | 398.2 | 398.2 | I-7 | 535 | 570 | 95 | 449.3 | 449.2 |
| C-1 | 535 | 575 | 99 | 373.2 | 373.2 | I-8 | 535 | 570 | 90 | 445.2 | 445.2 |
| C-2 | 535 | 575 | 98 | 398.2 | 398.2 | I-9 | 535 | 565 | 96 | 475.3 | 475.2 |
| C-3 | 535 | 570 | 95 | 385.2 | 385.2 | I-13 | 535 | 570 | 88 | 479.3 | 479.2 |
| C-4 | 532 | 570 | 97 | 447.1 | 447.1 | I-14 | 530 | 565 | 87 | 455.3 | 455.2 |
| C-7 | 535 | 575 | 93 | 405.2 | 405.2 | I-15 | 535 | 565 | 90 | 399.2 | 399.2 |
| C-8 | 535 | 575 | 92 | 401.2 | 401.1 | I-16 | 535 | 560 | 93 | 427.3 | 427.2 |
| C-9 | 530 | 570 | 93 | 431.2 | 431.2 | I-17 | 535 | 570 | 94 | 429.3 | 429.2 |
| C-13 | 555 | 575 | 97 | 435.2 | 435.2 | I-18 | 535 | 565 | 91 | 443.2 | 443.2 |
| C-15 | 535 | 575 | 90 | 355.2 | 355.2 | I-19 | 540 | 570 | 94 | 417.2 | 417.2 |

FIG. 11 (cont'd)

| CODE | $\lambda ab(nm)^a$ | $\lambda em(nm)^b$ | PURITY%$^c$ | MASS$^d$ (CALC.) | MASS$^e$ (FOUND) | CODE | $\lambda ab(nm)^a$ | $\lambda em(nm)^b$ | PURITY%$^c$ | MASS$^d$ (CALC.) | MASS$^e$ (FOUND) |
|---|---|---|---|---|---|---|---|---|---|---|---|
| C-16 | 530 | 570 | 91 | 383.2 | 383.2 | I-23 | 535 | 565 | 91 | 413.3 | 413.2 |
| C-17 | 535 | 575 | 93 | 385.1 | 385.2 | I-25 | 535 | 565 | 99 | 457.3 | 457.2 |
| C-18 | 535 | 575 | 91 | 399.2 | 399.1 | I-27 | 535 | 565 | 91 | 431.3 | 431.2 |
| C-19 | 540 | 575 | 95 | 373.2 | 373.1 | I-29 | 530 | 565 | 89 | 441.3 | 441.2 |
| C-20 | 540 | 575 | 94 | 389.1 | 389.1 | I-30 | 535 | 570 | 94 | 498.3 | 498.2 |
| C-21 | 540 | 585 | 90 | 383.2 | 383.1 | I-31 | 530 | 570 | 90 | 496.3 | 496.2 |
| C-22 | 535 | 570 | 95 | 510.3 | 510.2 | I-32 | 540 | 575 | 91 | 496.3 | 496.3 |
| C-23 | 535 | 570 | 92 | 369.2 | 369.2 | J-1 | 505 | 550 | 93 | 412.2 | 412.2 |
| C-24 | 535 | 570 | 99 | 415.2 | 415.1 | J-2 | 495 | 0 | 100 | 437.3 | 437.2 |
| C-25 | 530 | 560 | 93 | 413.2 | 413.2 | J-3 | 500 | 555 | 99 | 424.2 | 424.2 |
| C-26 | 540 | 570 | 91 | 403.2 | 403.1 | J-4 | 500 | 540 | 95 | 486.3 | 486.2 |
| C-27 | 535 | 570 | 90 | 387.2 | 387.1 | J-7 | 500 | 565 | 94 | 444.2 | 444.2 |
| C-29 | 530 | 570 | 95 | 397.2 | 397.2 | J-8 | 500 | 590 | 97 | 440.2 | 440.2 |
| C-30 | 535 | 560 | 97 | 454.3 | 454.2 | J-9 | 510 | 540 | 93 | 470.3 | 470.2 |
| C-31 | 540 | 565 | 96 | 452.3 | 452.2 | J-10 | 500 | 550 | 93 | 446.2 | 446.1 |
| C-32 | 540 | 565 | 98 | 452.3 | 452.2 | J-12 | 505 | 550 | 98 | 448.2 | 448.1 |
| D-7 | 500 | 530 | 88 | 338.1 | 338.1 | J-13 | 505 | 545 | 96 | 474.3 | 474.2 |
| D-8 | 500 | 530 | 96 | 334.1 | 334.1 | J-14 | 500 | 550 | 97 | 450.3 | 450.2 |

| CODE | λab(nm)[a] | λem(nm)[b] | PURITY%[c] | MASS[d] (CALC.) | MASS[e] (FOUND) | CODE | λab(nm)[a] | λem(nm)[b] | PURITY%[c] | MASS[d] (CALC.) | MASS[e] (FOUND) |
|---|---|---|---|---|---|---|---|---|---|---|---|
| D-9 | 500 | 535 | 90 | 364.1 | 364.1 | J-15 | 500 | 550 | 91 | 394.2 | 394.2 |
| D-13 | 500 | 530 | 96 | 368.1 | 368.1 | J-16 | 505 | 565 | 96 | 422.3 | 422.2 |
| D-17 | 500 | 530 | 92 | 318.1 | 318.1 | J-17 | 500 | 575 | 93 | 424.2 | 424.2 |
| D-18 | 500 | 530 | 90 | 332.1 | 332.1 | J-18 | 505 | 605 | 94 | 438.2 | 438.2 |
| D-23 | 490 | 525 | 95 | 302.1 | 302.1 | J-19 | 500 | 555 | 94 | 412.2 | 412.2 |
| D-25 | 495 | 525 | 90 | 346.1 | 346.1 | J-23 | 500 | 560 | 92 | 408.2 | 408.2 |
| D-27 | 495 | 530 | 91 | 320.1 | 320.1 | J-25 | 505 | 565 | 89 | 452.3 | 452.2 |
| D-29 | 495 | 530 | 96 | 330.1 | 330.1 | J-27 | 500 | 575 | 94 | 426.2 | 426.2 |
| E-1 | 490 | 545 | 90 | 346.2 | 346.1 | J-28 | 515 | 565 | 93 | 400.2 | 400.1 |
| E-2 | 480 | 550 | 86 | 371.2 | 371.2 | J-29 | 500 | 565 | 97 | 436.3 | 436.2 |
| E-3 | 485 | 545 | 93 | 358.2 | 358.2 | J-30 | 500 | 575 | 99 | 493.3 | 493.2 |
| E-4 | 480 | 545 | 90 | 420.2 | 420.2 | J-31 | 505 | 560 | 99 | 491.3 | 491.2 |
| E-7 | 485 | 545 | 95 | 378.2 | 378.2 | J-32 | 500 | 560 | 100 | 491.3 | 491.2 |
| E-8 | 485 | 550 | 91 | 374.2 | 374.1 | K-7 | 485 | 555 | 91 | 392.2 | 392.2 |
| E-9 | 485 | 550 | 91 | 404.2 | 404.2 | K-13 | 485 | 555 | 88 | 422.2 | 422.2 |
| E-10 | 495 | 550 | 91 | 380.1 | 380.1 | K-17 | 490 | 560 | 92 | 372.2 | 372.2 |
| E-13 | 475 | 540 | 98 | 408.2 | 408.2 | K-23 | 480 | 555 | 99 | 356.2 | 356.2 |
| E-14 | 480 | 550 | 92 | 384.2 | 384.2 | K-27 | 480 | 555 | 88 | 374.2 | 374.2 |

| CODE | λab(nm)a | λem(nm)b | PURITY%c | MASS d (CALC.) | MASS e (FOUND) | CODE | λab(nm)a | λem(nm)b | PURITY%c | MASS d (CALC.) | MASS e (FOUND) |
|---|---|---|---|---|---|---|---|---|---|---|---|
| E-15 | 485 | 550 | 88 | 328.2 | 328.2 | L-1 | 530 | 555 | 96 | 418.2 | 418.2 |
| E-16 | 480 | 545 | 87 | 356.2 | 356.2 | L-3 | 525 | 555 | 97 | 430.3 | 430.2 |
| E-17 | 490 | 545 | 90 | 358.2 | 358.2 | L-4 | 525 | 555 | 94 | 492.3 | 492.2 |
| E-18 | 485 | 550 | 85 | 372.2 | 372.2 | L-7 | 530 | 560 | 95 | 450.3 | 450.2 |
| E-19 | 485 | 545 | 91 | 346.2 | 346.1 | L-8 | 525 | 560 | 92 | 446.2 | 446.2 |
| E-20 | 485 | 550 | 89 | 362.1 | 362.1 | L-9 | 525 | 560 | 97 | 476.3 | 476.2 |
| E-21 | 490 | 545 | 92 | 356.2 | 356.2 | L-10 | 535 | 560 | 93 | 452.2 | 452.1 |
| E-23 | 485 | 545 | 99 | 342.2 | 342.2 | L-13 | 525 | 555 | 94 | 480.3 | 480.2 |
| E-24 | 486 | 545 | 95 | 388.2 | 388.1 | L-14 | 525 | 555 | 93 | 456.3 | 456.2 |
| E-25 | 480 | 545 | 98 | 386.2 | 386.2 | L-15 | 525 | 555 | 96 | 400.2 | 400.2 |
| E-26 | 485 | 545 | 85 | 376.2 | 376.1 | L-16 | 525 | 555 | 99 | 428.3 | 428.2 |
| E-27 | 480 | 545 | 94 | 360.2 | 360.2 | L-17 | 530 | 555 | 94 | 430.3 | 430.2 |
| E-29 | 485 | 550 | 89 | 370.2 | 370.2 | L-18 | 525 | 555 | 97 | 444.2 | 444.2 |
| F-1 | 515 | 540 | 91 | 333.1 | 333.2 | L-19 | 530 | 560 | 95 | 414.3 | 414.2 |
| F-3 | 510 | 540 | 94 | 345.2 | 345.1 | L-23 | 525 | 555 | 98 | 418.2 | 418.2 |
| F-4 | 500 | 540 | 95 | 407.2 | 407.1 | L-25 | 525 | 555 | 97 | 458.3 | 458.2 |
| F-7 | 510 | 540 | 88 | 365.2 | 365.2 | L-27 | 525 | 555 | 94 | 432.2 | 432.2 |
| F-8 | 505 | 545 | 90 | 361.1 | 361.1 | L-29 | 525 | 555 | 94 | 442.3 | 442.2 |

*FIG. 11 (cont'd)*

COMBINATORIAL ROSAMINE LIBRARY AND USES THEREOF

This application claims the benefit of U.S. Provisional Patent Application Ser. No. 60/844,176, filed Sep. 13, 2006, which is hereby incorporated by reference in its entirety.

FIELD OF THE INVENTION

The present invention is directed to a combinatorial rosamine library and uses thereof.

BACKGROUND OF THE INVENTION

Fluorescent compounds have been excellent tools for the sensitive and specific detection of a variety of analytes (De Silva et al., "Signaling Recognition Events with Fluorescent Sensors and Switches," *Chem Rev* 97:1515-1566 (1997)). While the rational approach in designing the fluorescent sensors was successful toward diverse small molecule analytes (Gabe et al., "Highly Sensitive Fluorescence Probes for Nitric Oxide Based on Boron Dipyrromethene Chromophore-Rational Design of Potentially Useful Bioimaging Fluorescence Probe," *J Am Chem Soc* 126:3357-3367 (2004); Chang et al., "A Selective, Cell-Permeable Optical Probe for Hydrogen Peroxide in Living Cells," *J Am Chem Soc* 126:15392-15393 (2004); Burdette et al., "Fluorescent Sensors for Zn(2+) Based on a Fluorescein Platform: Synthesis, Properties and Intracellular Distribution," *J Am Chem Soc* 123:7831-7841 (2001); Schneider et al., "Coupling Rational Design with Libraries Leads to the Production of an ATP Selective Chemosensor," *J Am Chem Soc* 122:542-543 (2000)), the combinatorial approach to fluorescent dyes has shown powerful advantages owing to a wide range of spectral and structural diversity, developing specific binders for macromolecule structures with a concomitant change of fluorescence properties (Rosania et al., "Combinatorial Approach to Organelle-Targeted Fluorescent Library Based on the Styryl Scaffold," *J Am Chem Soc* 125:1130-1131 (2003); Lee et al., "Development of Novel Cell-Permeable DNA Sensitive Dyes Using Combinatorial Synthesis and Cell-Based Screening," *Chem Commun (Camb)* 15:1852-1853 (2003); Li et al., "Solid-Phase Synthesis of Styryl Dyes and Their Application as Amyloid Sensors," *Angew Chem Int Ed Engl* 43(46):6331-6335 (2004); Li et al., "RNA-Selective, Live Cell Imaging Probes for Studying Nuclear Structure and Function," *Chem Biol* 13(6):615-623 (2006)).

The present invention is directed to an improved class of fluorescent compounds.

SUMMARY OF THE INVENTION

The present invention relates to a method of producing a rosamine derivative compound of the formula:

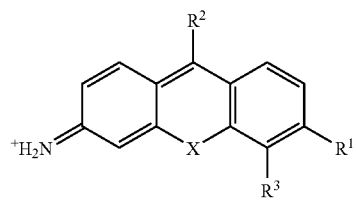

wherein
X is O, $NR^4$, or S;

$R_1$ is $NR^4R^5$, OH, $NR^4R^6$, or

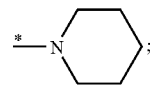

$R^2$ is substituted or unsubstituted phenyl, napthyl,

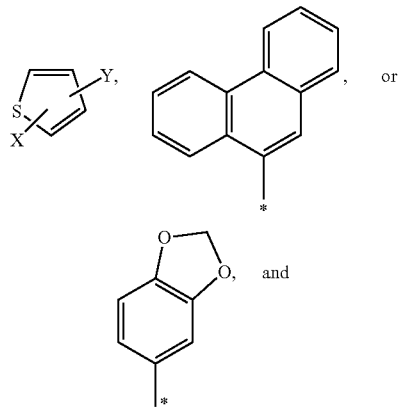

wherein the substituted form of $R^2$ has one or more of the following independently selected substituents: halogen, $NR^4R^5$, $OR^7$, $SR^4$, aryl, $C_1$ to $C_6$ alkyl,

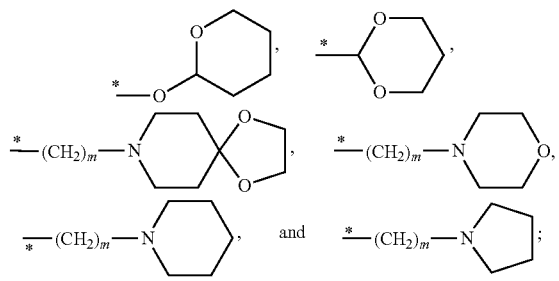

$R^3$ is H or with $R^1$ collectively forms a fused ring of the structure of

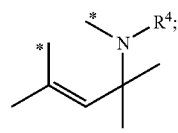

$R^4$ is H or $C_1$ to $C_6$ alkyl;
$R^5$ is H, $C_1$ to $C_6$ alkyl, or with $R^4$ collectively forms a ring structure;
$R^6$ is $(CH_2)_n NR^4R^8$;
$R^7$ is H, $C_1$ to $C_6$ alkyl, or aryl;
$R^8$ is H or $C_1$ to $C_6$ alkyl;
Y is alkyl or halogen;
n is 1 to 3;
m is 0 to 3; and
*is a site on a substituent which binds to the rosamine derivative compound.

The method includes providing a first intermediate compound of the formula:

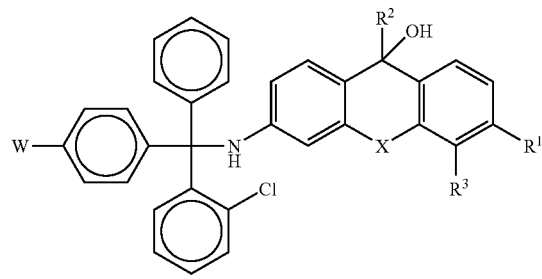

where:
W is a solid support.
The first intermediate compound is reacted under conditions effective to produce the rosamine derivative compound.

The present invention also relates to a rosamine derivative compound of the formula:

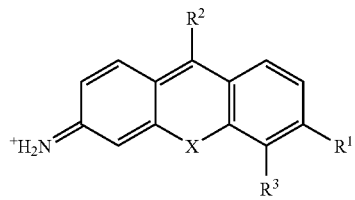

wherein
X is O, $NR^4$, or S;
$R_1$ is $NR^4R^5$, OH, $NR^4R^6$, or

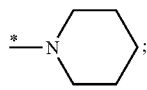

$R^2$ is substituted or unsubstituted phenyl, napthyl,

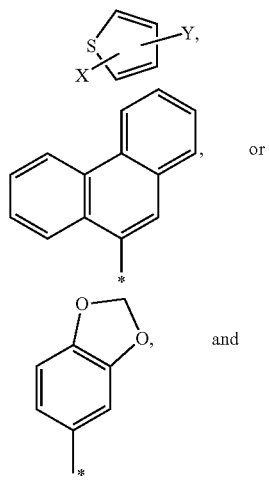

wherein the substituted form of $R^2$ has one or more of the following independently selected substituents: halogen, $NR^4R^5$, $OR^7$, $SR^4$, aryl, $C_1$ to $C_6$ alkyl,

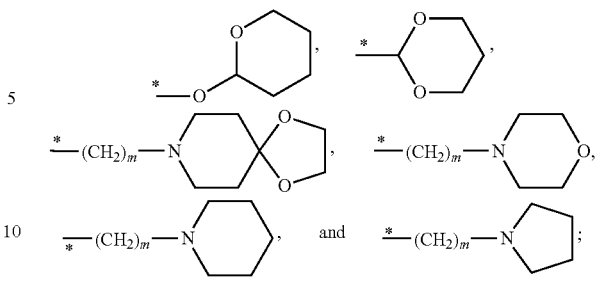

$R^3$ is H or with $R^1$ collectively forms a fused ring of the structure of

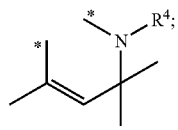

$R^4$ is H or $C_1$ to $C_6$ alkyl;
$R^5$ is H, $C_1$ to $C_6$ alkyl, or with $R^4$ collectively forms a ring structure;
$R^6$ is $(CH_2)_n NR^4R^8$;
$R^7$ is H, $C_1$ to $C_6$ alkyl, or aryl;
$R^8$ is H or $C_1$ to $C_6$ alkyl;
Y is alkyl or halogen;
n is 1 to 3;
m is 0 to 3; and
\*is a site on a substituent which binds to the rosamine derivative compound.

The present invention also relates to a method of detecting the presence, if any, of a target molecule in a sample. This involves providing a sample potentially containing a target molecule and the rosamine derivative compound of the present invention. The rosamine derivative compound has a first fluorescent characteristic when bound to the target molecule and a second fluorescent characteristic in an unbound state. The rosamine derivative compound is contacted with the sample under conditions effective to permit binding of any target molecule present in the sample to the rosamine derivative compound, where the presence of the target molecule in the sample is detected as a function of the fluorescence characteristic of the rosamine derivative compound, where the presence of the target molecule is indicated by detection of the first fluorescent characteristic while the absence of the target molecule is indicated by detection of the second fluorescence characteristic.

Another aspect of the present invention relates to a method of imaging cells. This involves providing cells to be imaged and the rosamine derivative compound of the present invention. The rosamine derivative compound is contacted with the cells to be imaged under conditions effective to permit binding of the rosamine derivative compound to the cells. The cells are exposed to activating radiation, where any of the rosamine derivative compound bound to the cell fluoresces. As a result, an image of the cells based on their fluorescent emission is produced.

Rhodamine is a highly favored scaffold for cellular imaging and small molecule analytes sensing, due to advantageous photophysical properties such as high extinction coefficient and quantum yield, low toxicity, high photostability and pH-insensitivity, and relatively long emission wavelength (>500 nm) (Haugland, R. P. *Handbook of Fluorescent Probes and Research Chemicals*, 9th ed.; Molecular Probes: Eugene, Oreg. (2002), which is hereby incorporated by reference in its entirety). Rhodamine derivatives are widely used for labeling DNA, RNA, and proteins, but often suffered fluorescence quenching when labeling on protein, (Haugland, R. P. *Handbook of Fluorescent Probes and Research Chemicals*, 9th ed.; Molecular Probes: Eugene, Oreg., 2002; Ravdin et al., "Fluorescent Tetramethyl Rhodamine Derivatives of Alpha-Bungarotoxin: Preparation, Separation, and Characterization," *Anal Biochem* 80:585-592 (1977), which are hereby incorporated by reference in their entirety), or almost no intensity change upon binding with peptide, (Marks et al., "In Vivo Targeting of Organic Calcium Sensors via Genetically Selected Peptides," *Chem Biol* 11(3):347-356 (2004); Rozinov et al., "Evolution of Peptides that Modulate the Spectral Qualities of Bound, Small-Molecule Fluorophores," *Chem Biol* 5(12):713-728 (1998), which are hereby incorporated by reference in their entirety), probably due to its rigid core structure with a high quantum yield. Therefore, it is envisioned that the introduction of structural flexibility and diversity on the rhodamine scaffold would generate a set of sensor candidates of which fluorescence intensity can be controlled by a binding event. The first combinatorial approach to a rosamine library is reported here and the potential of this library to find a selective sensor to a specific analytes is demonstrated.

BRIEF DESCRIPTION OF THE DRAWINGS

FIGS. 6 A-D show the characterization of the specific rosamine molecule, A4 in Table 1. FIG. 6A shows the structure and the images of the solution with and without UV irradiation. FIG. 6B shows the LCMS trace in 250 nm and mass spectrum with a value of 379.4 found (calculated: 379.14). FIG. 6C shows the absorbance spectrum with a $\lambda_{max}$ of 500 nm. FIG. 6D shows the fluorescence emission spectrum with a $\lambda_{max}$ of 530 nm, excitation 480 nm.

FIG. 8 shows the screening of 240 rosamine libraries with 47 analytes. Lof(F) is a logarithm value of fluorescence intensity change upon addition of the analyte. y-axis: each rosamine molecule, and x-axis: each analyte.

FIG. 10 A-B shows the fluorescence response of the specific rosamine molecules (J and L in Table 1) toward different analytes.

FIG. 11 shows the absorbance, fluorescent wavelength, and purity for the library of rosamine derivative compounds of the present invention.

FIG. 14A shows cells stained with H22 (3 μM) for 15 min. FIG. 14B shows cells supplemented with lipoic acid (250 μM) for 48 hr and stained with H22 for 15 min. Subsequently, α-lipoic acid-supplemented cells stained with H22 was incubated with NMM (1 mM) (FIG. 14C) or Diamide (50 μM) (FIG. 14D) for 20 min at room temperature.

DETAILED DESCRIPTION OF THE INVENTION

Figure 1:
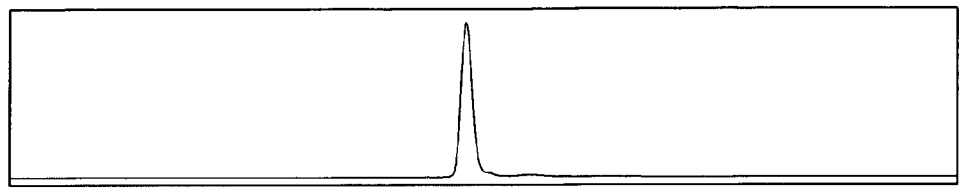
FIG. 1 shows the structure and HPLC trace of compound B1 in Table 1 (i.e. the rosamine derivative compound which is the reaction product of structure B from the listing of building block $T^1$ structures in Table 1 and structure 1 from the listing of $T^2$ structures in Table 1) in absorption of 500 nm and 250 nm and mass spectrum.
Figure 1:
Figure 1:
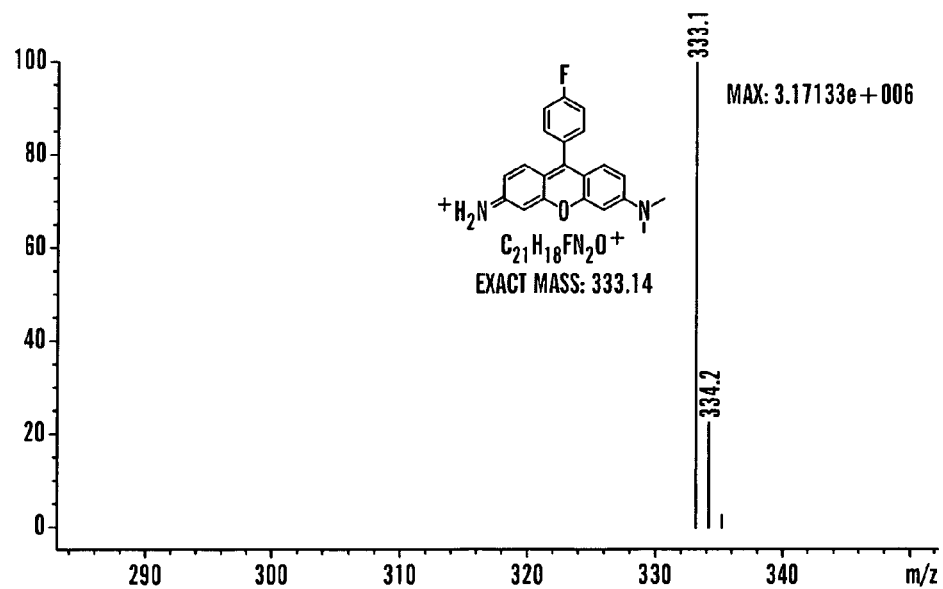
Figure 2:
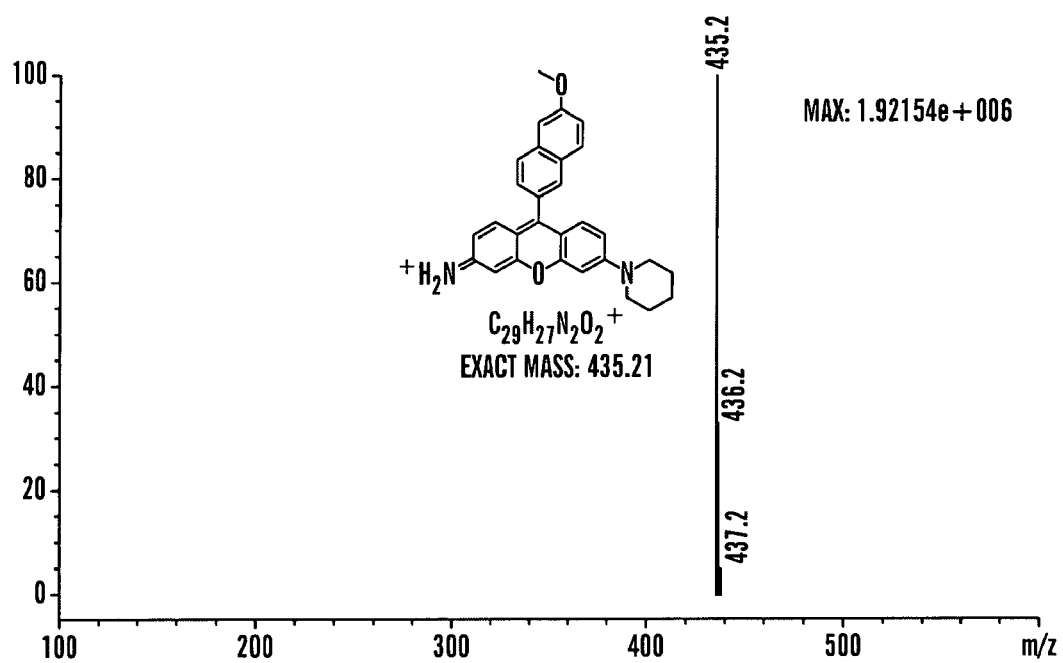
FIG. 2 shows the structure and HPLC trace of compound C13 in Table 1 in absorption of 530 nm and 250 nm mass spectrum.
Figure 3:
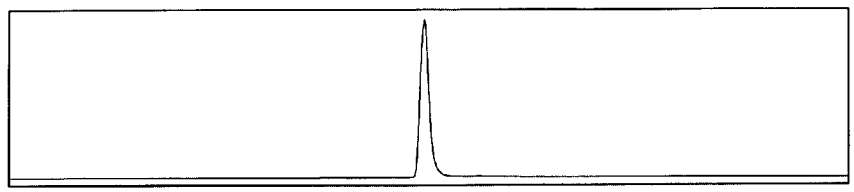
FIG. 3 shows the structure and HPLC trace of compound G9 in Table 1 in absorption of 520 nm and 250 nm mass spectrum.
Figure 3:
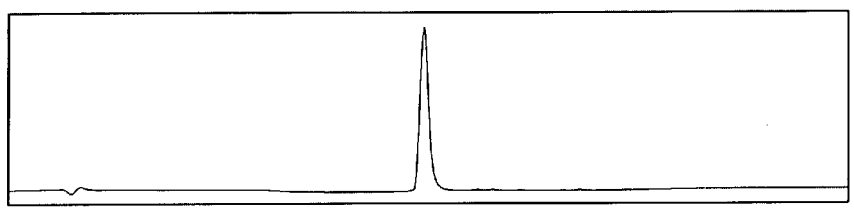
Figure 3:
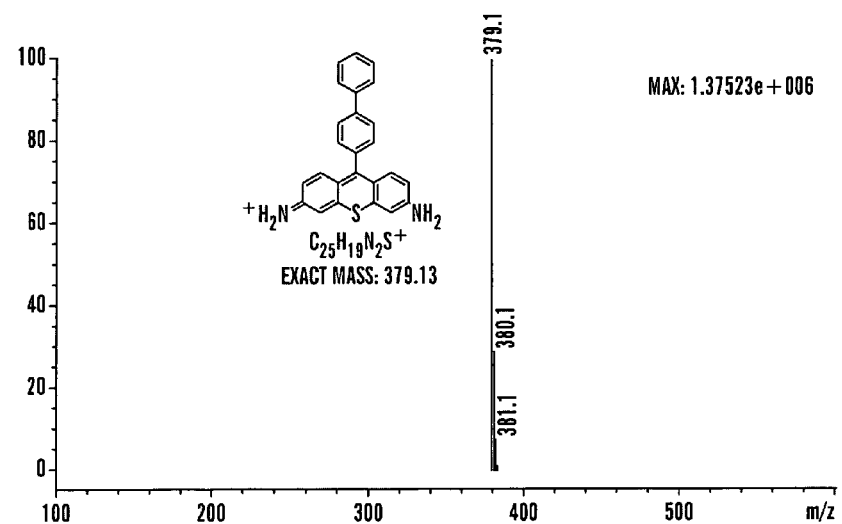
Figure 4:
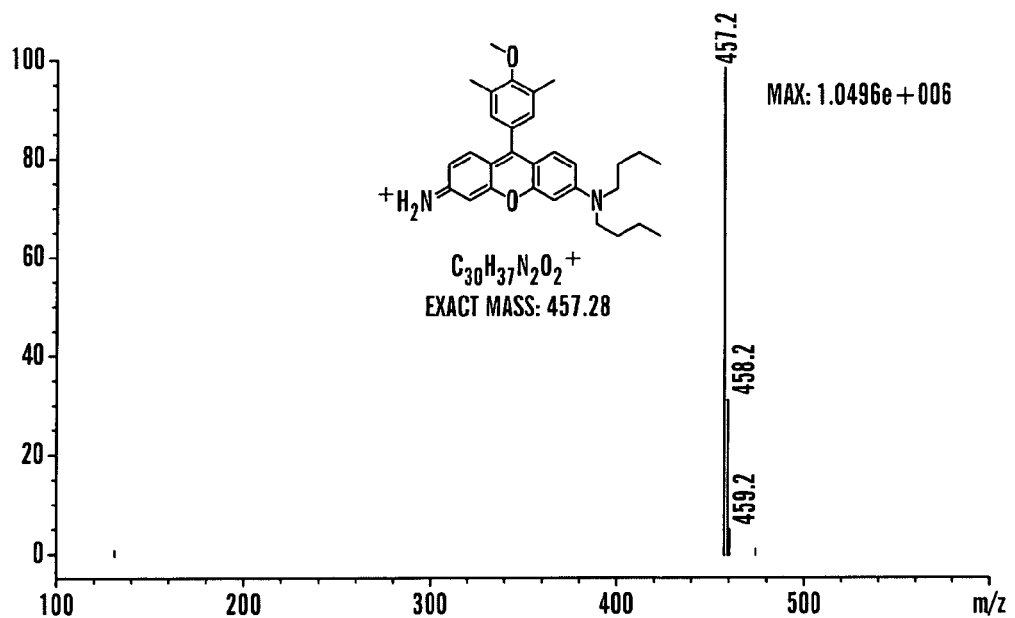
FIG. 4 shows the structure and HPLC trace of compound 125 in Table 1 in absorption of 480 nm and 250 nm mass spectrum.
Figure 5:
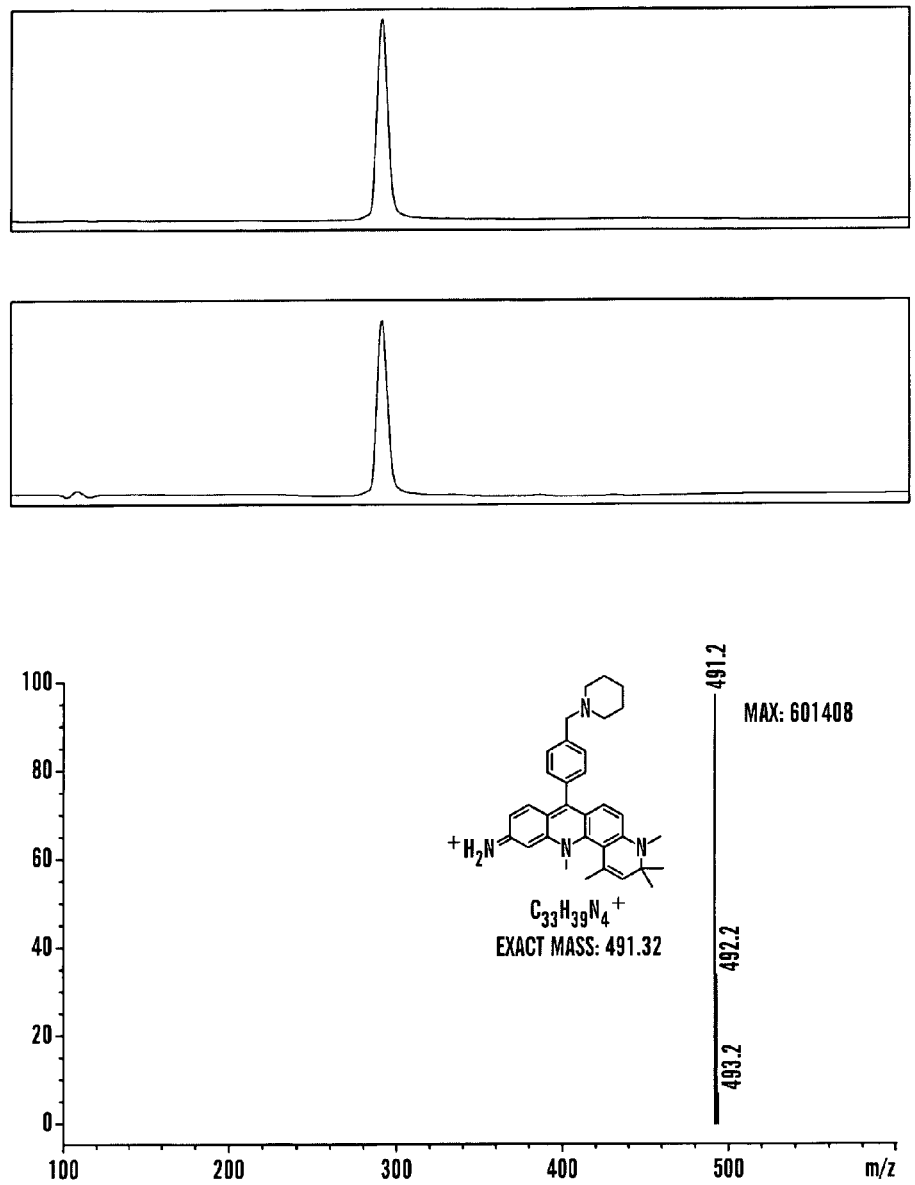
FIG. 5 shows the structure and HPLC trace of compound J32 in Table 1 in absorption of 530 nm and 250 nm mass spectrum.
Figure 7:
FIG. 7 shows the different localization of rosamine molecules (nucleoli, nucleus, lysosome, mitochondria, vesicle, and cytoplasm: B28, B21, L14, A4, J7, and J9 in Table 1).
Figure 7:
Figure 7:
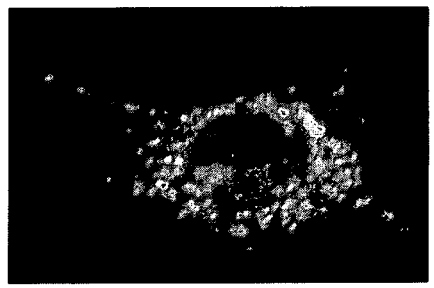
Figure 7:
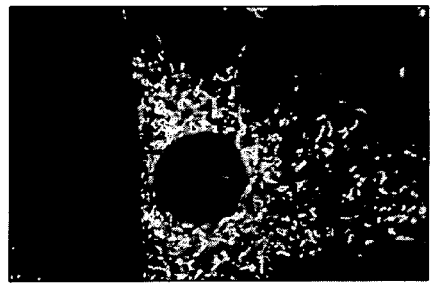
Figure 7:
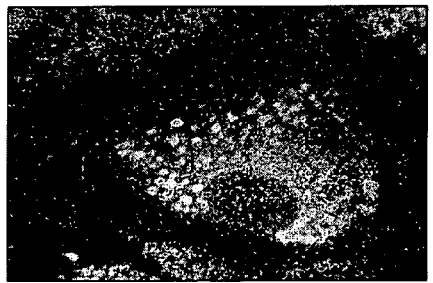
Figure 7:
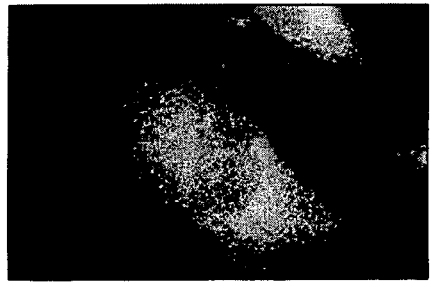
Figure 9:
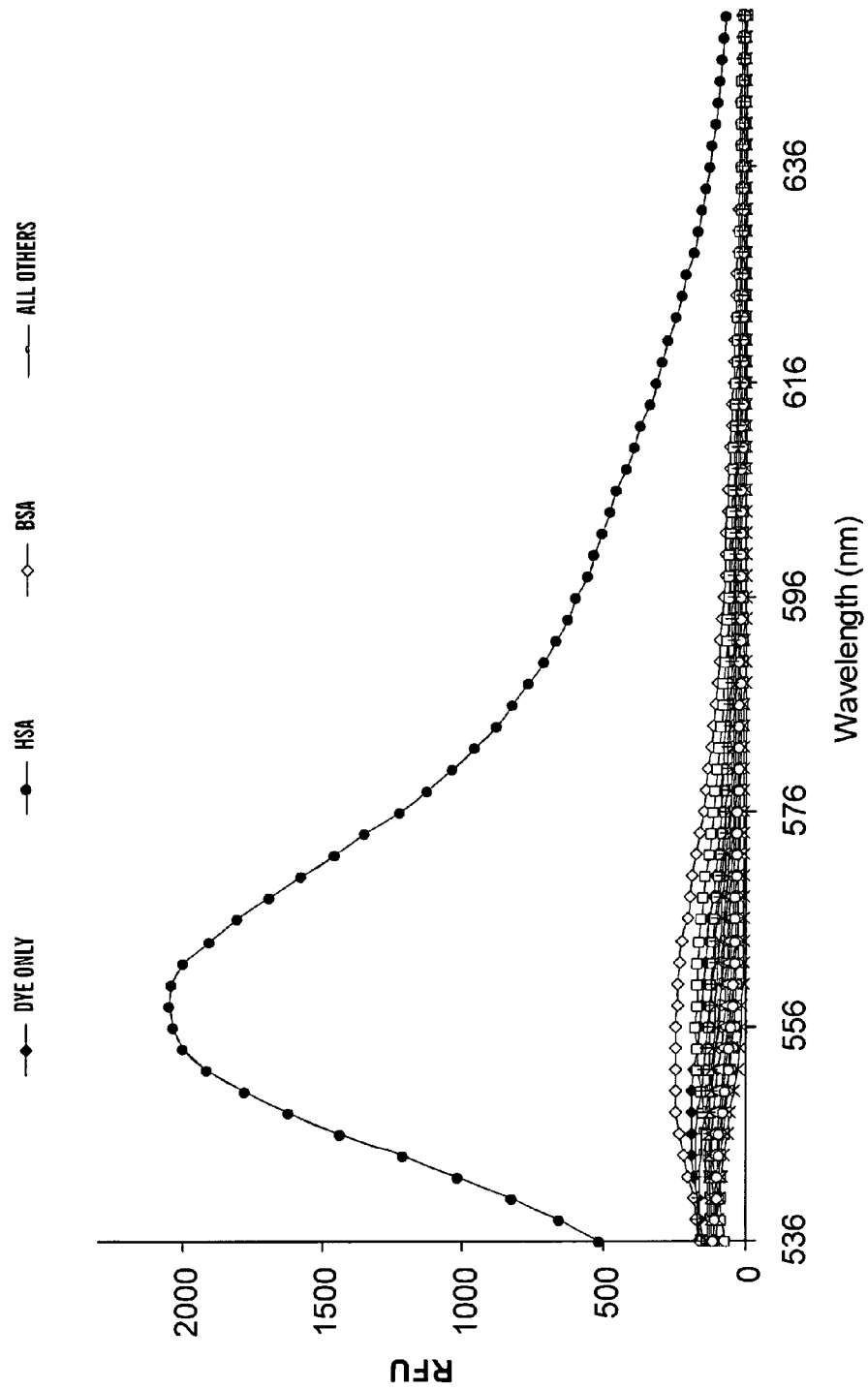
FIG. 9 shows the fluorescence emission response of G13 in Table 1 in the presence of 13 different proteins: control, HSA, BSA, dsDNA, RNA, peroxidase, cellulase A, protease A, lipase, lysozyme, papain, heparin, hemoglobin, and hemicellulase). G13 (10 μM) and all proteins (0.5 mg/mL) in HEPES (10 mM, pH=7.4) show a 12.5 fold change with HSA in 556 nm.

The present invention relates to a method of producing a rosamine derivative compound of the formula:

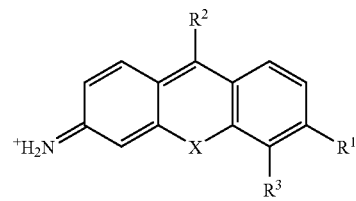

wherein

X is O, $NR^4$, or S;

$R_1$ is $NR^4R^5$, OH, $NR^4R^6$, or

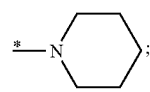

$R^2$ is substituted or unsubstituted phenyl, napthyl,

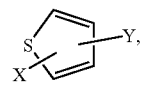

-continued

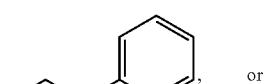, or

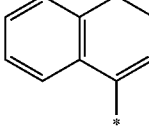 and

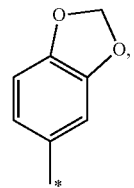

wherein the substituted form of $R^2$ has one or more of the following independently selected substituents: halogen, $NR^4R^5$, $OR^7$, $SR^4$, aryl, $C_1$ to $C_6$ alkyl,

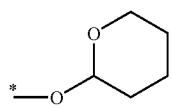

(this substituent is from building block 5 of the $T^2$ building blocks, and the product will be the deprotected one, giving

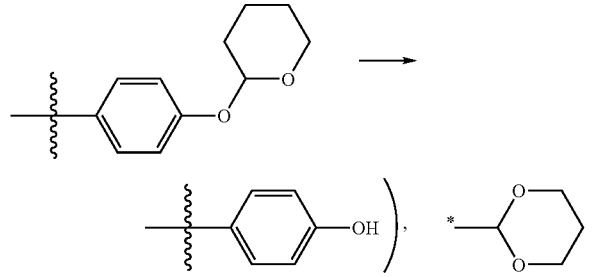

(this substituent is from building block 21 of the $T^2$ building blocks, and the product will be the deprotected one, giving

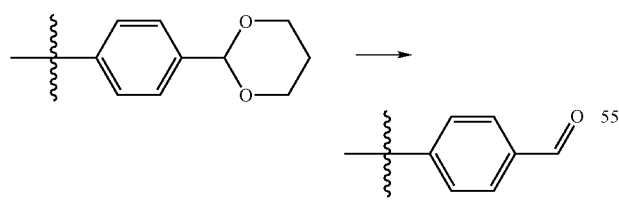

the deprotection occurred in the final step with TFA),

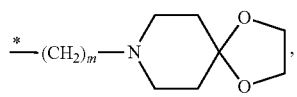 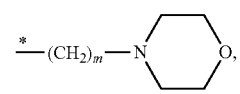

-continued

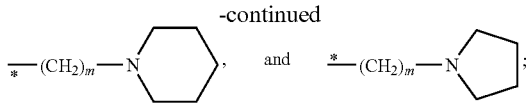

$R^3$ is H or with $R^1$ collectively forms a fused ring of the structure of

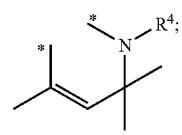

$R^4$ is H or $C_1$ to $C_6$ alkyl;
$R^5$ is H, $C_1$ to $C_6$ alkyl, or with $R^4$ collectively forms a ring structure;
$R^6$ is $(CH_2)NR^4R^8$;
$R^7$ is H, $C_1$ to $C_6$ alkyl, or aryl;
$R^8$ is H or $C_1$ to $C_6$ alkyl;
Y is alkyl or halogen;
n is 1 to 3;
m is 0 to 3; and
*is a site on a substituent which binds to the rosamine derivative compound.

The method includes providing a first intermediate compound of the formula:

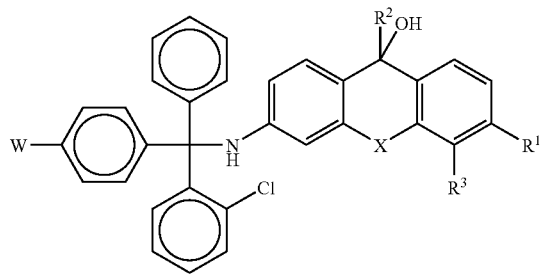

where:
W is a solid support.

The first intermediate compound is reacted under conditions effective to produce the rosamine derivative compound.

In one embodiment of the present invention, conditions effective to produce the rosamine derivative compound include carrying out a cleavage reaction.

The first intermediate compound may be produced by providing a second intermediate compound of the formula:

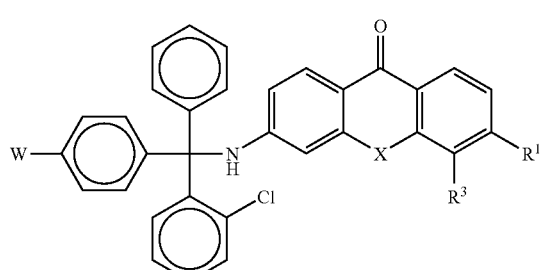

and reacting it under conditions to produce the first intermediate compound. These conditions may include carrying out a Grignard reaction with a reagent corresponding to $T^2$, which is listed in Table 1.

The second intermediate compound can be provided by providing a third intermediate compound of the formula:

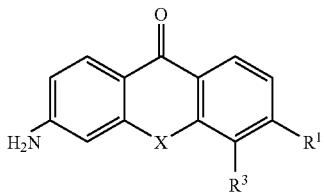

and reacting it under conditions effective to produce the second intermediate compound. These conditions may include reacting the third intermediate compound (corresponding to $T^1$ in Table 1) with a chlorotrityl chloride resin.

The third intermediate compound may be produced by providing a fourth intermediate compound of the formula:

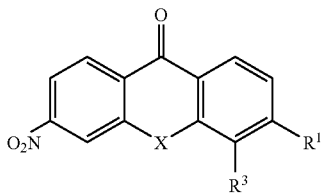

and reacting it under conditions to produce the third intermediate compound.

The fourth intermediate compound can be produced by providing a fifth intermediate compound of the formula:

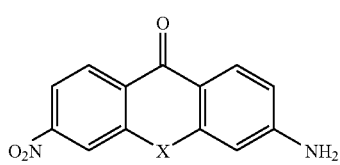

and reacting it under conditions to produce the fourth intermediate compound.

The fifth intermediate compound may be produced by providing a first starting material of the formula:

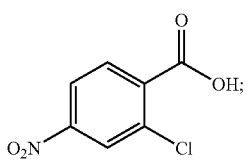

providing a second starting material of the formula:

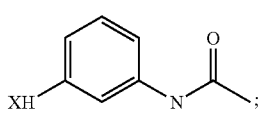

and reacting the first starting material and the second starting material under conditions effective to produce the fifth intermediate compound.

Most rhodamine derivatives including rosamine (rhodamine derivative without 2'-carboxylic acid) (Jiao et al., "Microwave-Assisted Syntheses of Regioisomerically Pure Bromorhodamine Derivatives," *Organic Lett* 5:3675-3677 (2003), which is hereby incorporated by reference in its entirety), have been prepared by individual condensation reaction under a strong acidic condition, (U.S. Pat. No. 5,686,261, to Zhang; Liu et al., "Rational Design and Synthesis of a Novel Class of Highly Fluorescent Rhodamine Dyes that Have Strong Absorption at Long Wavelengths," *Tetrahedron Lett* 44:4355-4359 (2003); Jiao et al., "Microwave-Assisted Syntheses of Regioisomerically Pure Bromorhodamine Derivatives," *Organic Lett* 5:3675-3677 (2003); Han et al., "Microwave-Assisted Functionalization of Bromo-Fluorescein and Bromorhodamine Derivatives," *Tetrahedron Lett* 44:9359-9362 (2003); and Felton et al., "Chromatographically Pure Fluorescein and Tetramethylrhodamine Isothiocyanates,"*Anal Biochem* 2:178-180 (1961), which are hereby incorporated in their entirety), requiring difficult or tedious purification, which is a serious bottleneck for library generation. Thus, to incorporate solid phase chemistry to generate the final product has been examined, circumventing acidic reflux condition and time-consuming purification steps. In particular, a rosamine structure was chosen to introduce the flexibility since the rotation of 9-phenyl ring without a 2'-substituent was suspected to induce the fluorescence change on the similar xanthene structure (Urano et al., "Evolution of Fluorescein as a Platform for Finely Tunable Fluorescence Probes," *J Am Chem Soc* 127:4888-4894 (2005), which is hereby incorporated in its entirety).

As shown in Table 1, two diversities ($T^1$ and $T^2$) were introduced successively, and one amino-functionality of the xanthene core was used as a linker to the resin (Scheme 1). Initially, three different 3-amino-6-nitro-9H-xanthone derivatives (S3, Y=O, NH, S) were synthesized that allowed the selective modification on the 3-amino position, and the 6-nitro group was utilized as a linker after reduction to amino group. Therefore, twelve different unsymmetrical xanthone derivatives (S5, $T^1$ building blocks, A-L in Table 1) containing different sizes and functionalities in addition to oxygen, sulfur, and nitrogen bridges were synthesized. Each intermediate was loaded on the 2-chlorotrityl chloride resin (S6) and heated with 33 different Grignard reagents for 2-4 days for the second diversity ($T^2$ building block in Table 1) ($T^1$ building block (D) proceeded t-butyldimethylsilyl group protection after loading on the resin, then Grignard reaction. Among $T^2$ building blocks, acetal protecting groups of 5 and 21 were removed after the Grignard reaction). The successive acidic cleavage (1% TFA in dichloromethane) from the resin resulted in the dehydration, giving the fully conjugated rosamine derivatives. All compounds in the library were characterized by HPLC-MS for the identification and purity (average purity is 93% at 250 nm, See FIGS. 1-11). 240 compounds have been prepared in this approach, having a relatively wide range of structural and spectral diversities (Excitation ranges from 480-545 nm and emission ranges from 530-605 nm). The quantum yield highly varies from 0.00025 to 0.89 in PBS (10 mM). Modification on $T^1$ was changing the excitation and emission maximum wavelength as well as fluorescence intensity while the modification on $T^2$ was slightly changing the excitation and emission maximum wavelength, but largely changing fluorescence intensity depending on the substituents.

The present invention also relates to a rosamine derivative compound of the formula:

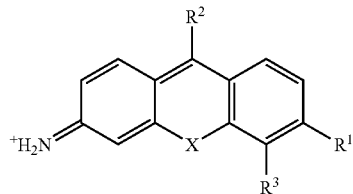

wherein
X is O, NR$^4$, or S;
R$_1$ is NR$^4$R$^5$, OH, NR$^4$R$^6$, or

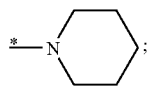

R$^2$ is substituted or unsubstituted phenyl, napthyl,

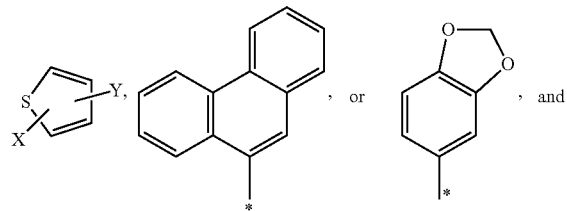

wherein the substituted form of R$^2$ has one or more of the following independently selected substituents: halogen, NR$^4$R$^5$, OR$^7$, SR$^4$, aryl, C$_1$ to C$_6$ alkyl,

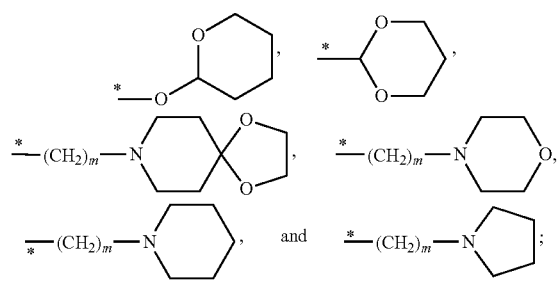

R$^3$ is H or with R$^1$ collectively forms a fused ring of the structure of

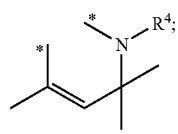

R$^4$ is H or C$_1$ to C$_6$ alkyl;
R$^5$ is H, C$_1$ to C$_6$ alkyl, or with R$^4$ collectively forms a ring structure;
R$^6$ is (CH$_2$)$_n$NR$^4$R$^8$;
R$^7$ is H, C$_1$ to C$_6$ alkyl, or aryl;

R$^8$ is H or C$_1$ to C$_6$ alkyl;
Y is alkyl or halogen;
n is 1 to 3;
m is 0 to 3; and
*is a site on a substituent which binds to the rosamine derivative compound.

As used above, and throughout the description of the present invention, the following terms, unless otherwise indicated, shall be understood to have the following meanings:

The term "alkyl" means an aliphatic hydrocarbon group which may be straight or branched having about 1 to about 6 carbon atoms in the chain. Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, and 3-pentyl.

The term "aryl" means an aromatic monocyclic or multi-cyclic ring system of 6 to about 14 carbon atoms, preferably of 6 to about 10 carbon atoms. Representative aryl groups include phenyl and naphthyl.

The term "halogen" means fluoro, chloro, bromo, or iodo.

The term "substituted" or "substitution" of an atom means that one or more hydrogen on the designated atom is replaced with a selection from the indicated group, provided that the designated atom's normal valency is not exceeded. "Unsubstituted" atoms bear all of the hydrogen atoms dictated by their valency. When a substituent is keto (i.e., =O), then 2 hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The fluorescent library is based on a rosamine scaffold including rosamine, thio-rosamine, and acridine structures, and the synthetic scheme is in Scheme 1.

TABLE 1

T$^1$ Building Block (S5):

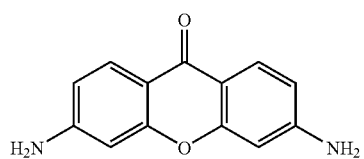

A

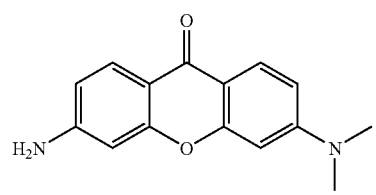

B

TABLE 1-continued
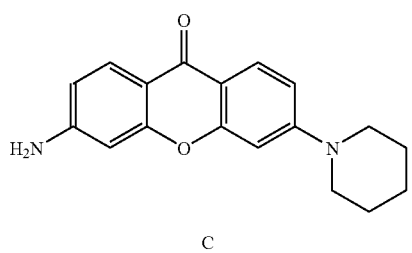
C
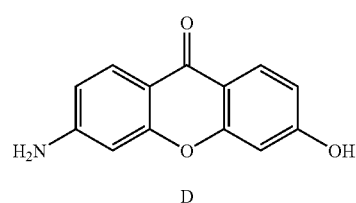
D
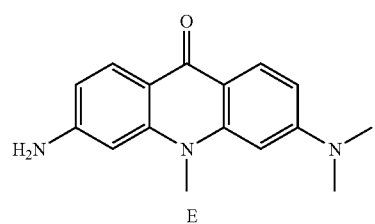
E
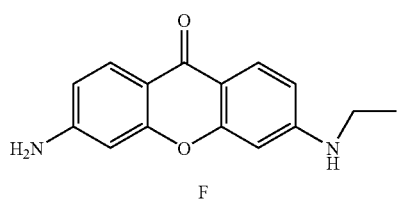
F
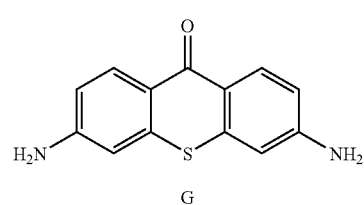
G
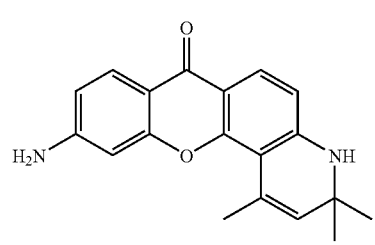
H
TABLE 1-continued
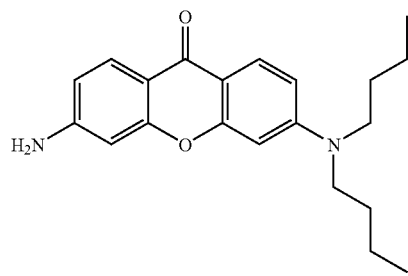
I
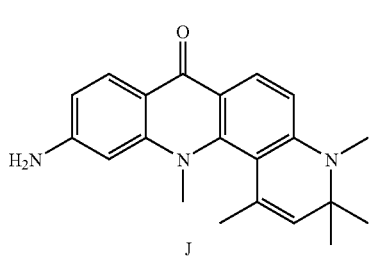
J
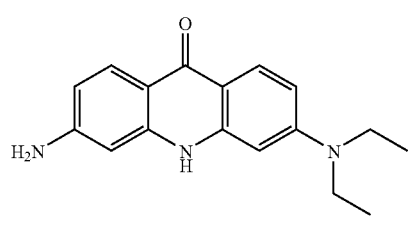
K
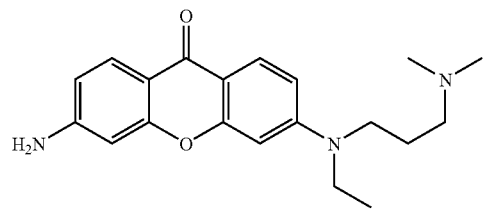
L
T² Building Block:
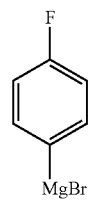
1
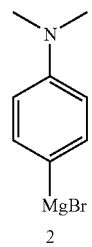
2

TABLE 1-continued
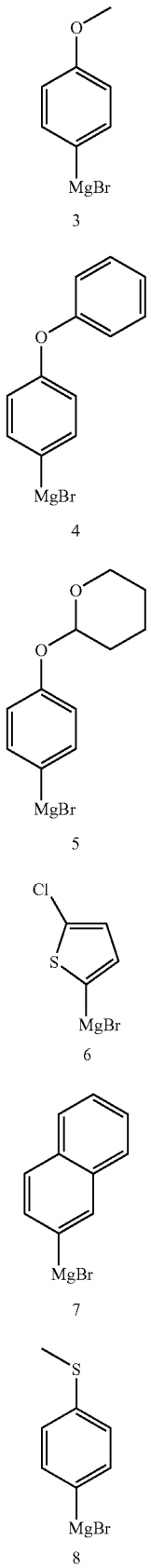
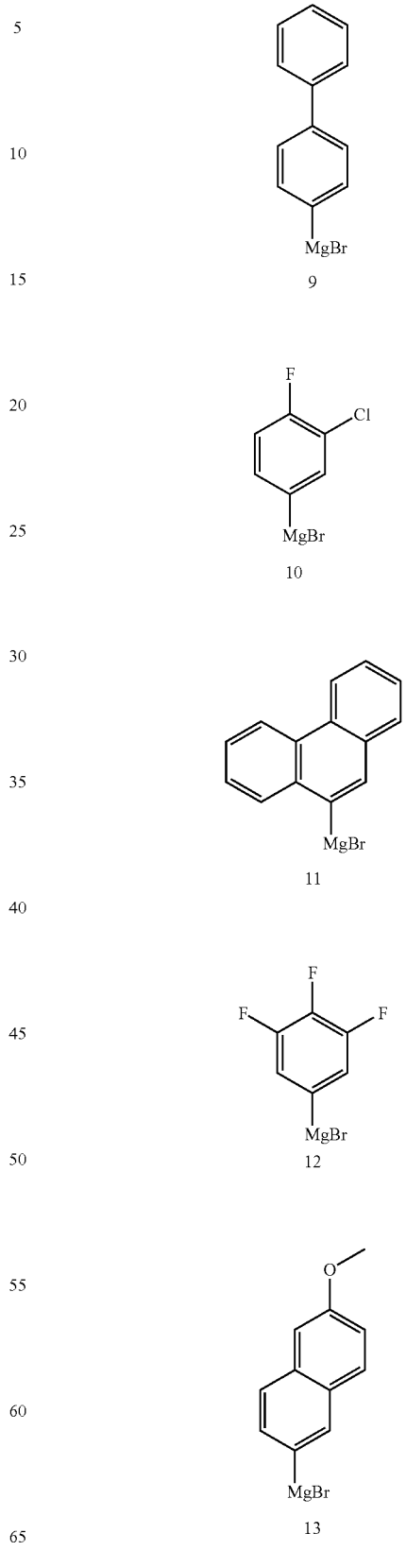

TABLE 1-continued
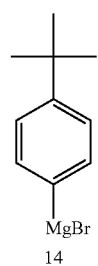
14
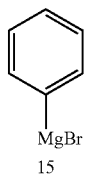
15
16
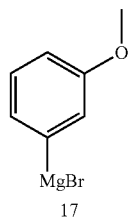
17
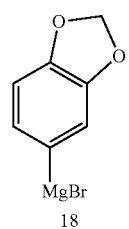
18
19
20
TABLE 1-continued
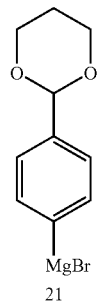
21
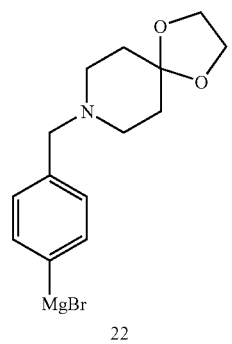
22
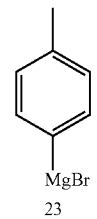
23
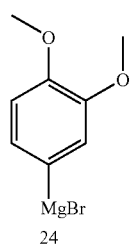
24
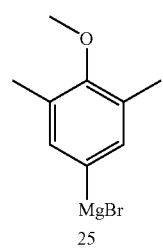
25
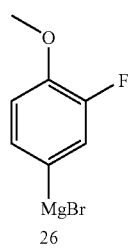
26

TABLE 1-continued
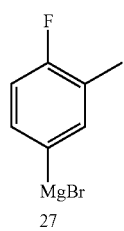
27
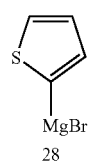
28
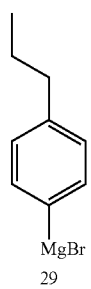
29
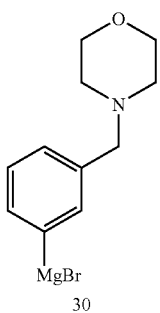
30
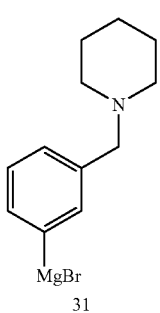
31
TABLE 1-continued
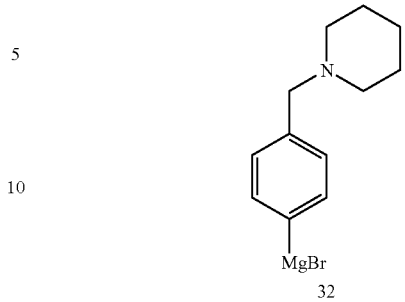
32
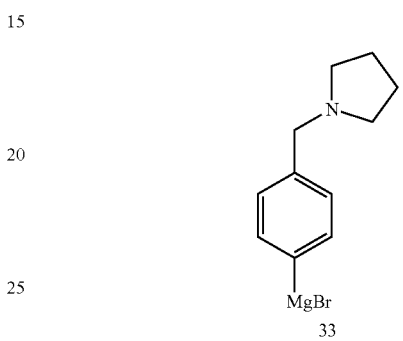
33
Scheme 1
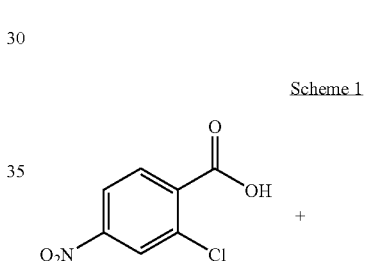
S1
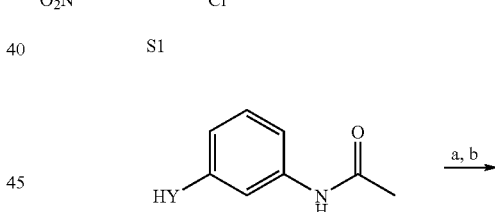
S2 Y = O, S, NH
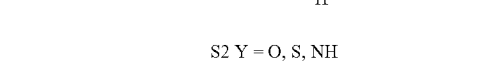 a, b
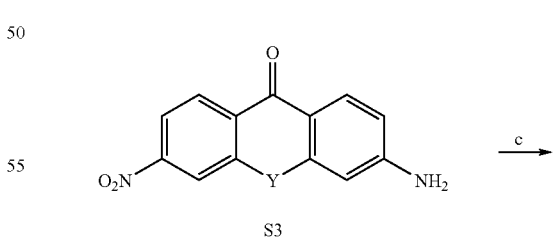
S3
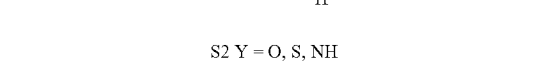 c
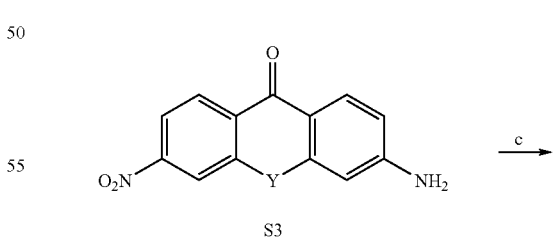
S4 X = O, S, NH or NCH₃
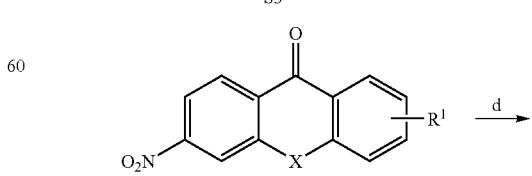 d

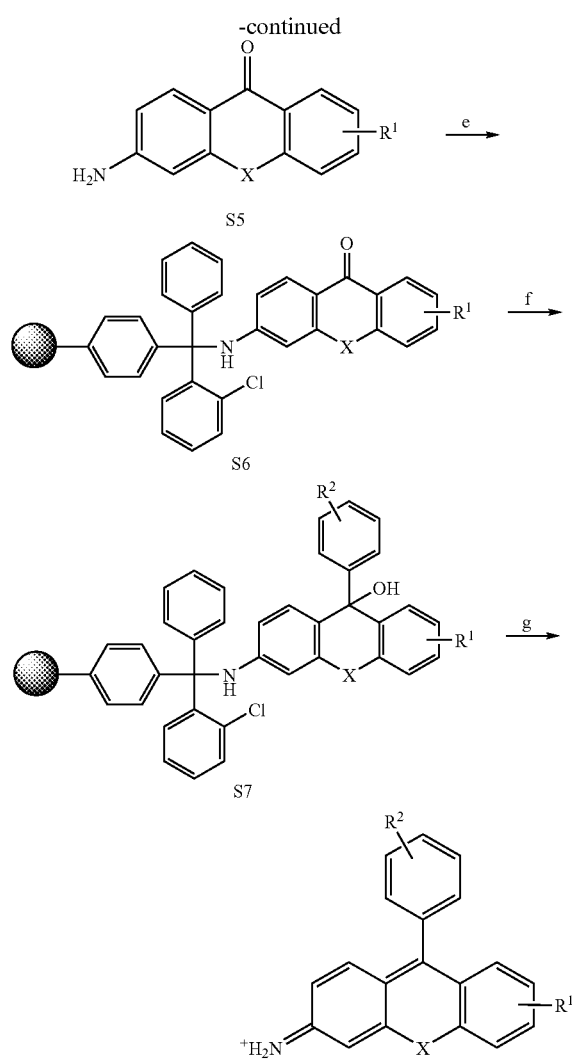

Synthesis generating rosamine-like library and building blocks;
a) K$_2$CO$_3$, Cu, DMF, 130° C.; b) H$_2$SO$_4$, 80° C.; c) modification for T$^1$ (see the section "Synthesis of all the intermediate" for each reaction);
d) SnCl$_2$, EtOH, 90° C.; e) 3-chloro-trityl chloride resin, pyr, CH$_2$Cl$_2$/DMF;
f) R$^2$ Grignard reagent, THF; g) 1% TFA, CH$_2$Cl$_2$ The present invention also relates to a method of detecting the presence, if any, of a target molecule in a sample. This involves providing a sample potentially containing a target molecule and the rosamine derivative compound. The rosamine derivative compound has a first fluorescent characteristic when bound to the target molecule and a second fluorescent characteristic in an unbound state. The rosamine derivative compound is contacted with the sample under conditions effective to permit binding of any target molecule present in the sample to the rosamine derivative compound, where the presence of the target molecule in sample is detected as a function of the fluorescence characteristic of the rosamine derivative compound. The presence of the target molecule is indicated by detection of the first fluorescent characteristic, while the absence of the target molecule is indicated by detection of the second fluorescence characteristic.

The tagged small molecule library of the present invention may be used in facilitating the drug development procedure. As the number and identification of drug targets (proteins) and gene functions continues to increase, there will be an increasing role for chemical genetics. Chemical library screening targets a specific gene product and is used to find an interesting phenotypic change. One chemical compound may specifically inhibit or activate one or more multiple target proteins. A large number of molecules are synthesized into a library, screened, and then the lead compound is modified by a target molecule (with fluorescence) for identification of the target protein.

Different cell lines can be utilized, including human normal and cancer cells, muscle cells, and embryonic cells to investigate any potential phenotype when treated with rosamine derivative compounds. A particular phenotype may be monitored through a confocal microscope or distinct fluorescence changes. The lead compound is attached to agarose or modified with a chemical or photoaffinity tag for isolation and identification of the target protein.

Another aspect of the present invention relates to a method of imaging cells. This involves providing cells to be imaged and the rosamine derivative compound of the present invention. The rosamine derivative compound is contacted with the cells to be imaged under conditions effective to permit binding of the rosamine derivative compound to the cells. The cells are exposed to activating radiation, where any of the rosamine derivative compound bound to the cell fluoresces. As a result, an image of the cells based on their fluorescent emission is produced.

This procedure can be carried out, for example, by growing HeLa and 3T3 cells on the glass bottom of 96-well black plates. Each rosamine derivative compound is added to the cell culture well at the desired concentration. An optical fluorescence microscope with a 100× oil immersion objective is used for the imaging experiment to detect the localization or the specific position of each compound in the cell.

Library based development of new optical imaging probes with optimized properties may be applied for single-molecule resolution optical imaging in living cells. The present invention utilizes libraries of rosamine-type fluorophores for this purpose.

EXAMPLES

The following examples are provided to illustrate embodiments of the present invention but are by no means intended to limit its scope.

Examples 1-15

Synthesis of all the Intermediates

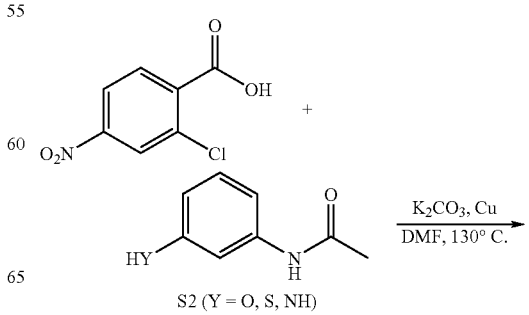

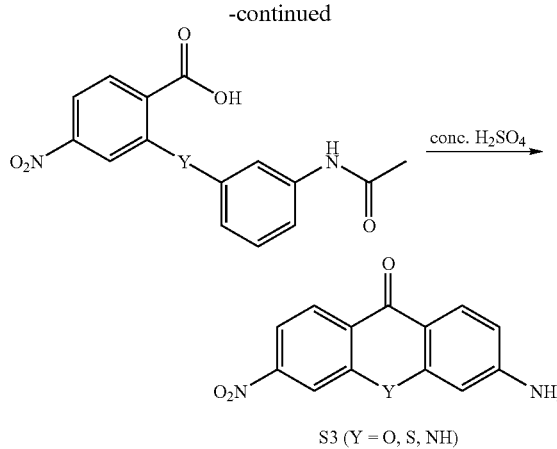

S3 (Y = O, S, NH)

Example 1

Synthesis of 3-Amino-6-Nitro-9H-Xanthone (S3, Y=O)

To a solution of 2-chloro-4-nitrobenzoic acid (3 g, 14.88 mmol) in DMF (40 mL) was added 3-3'-acetamidolphenol (2.47 g, 16.38 mmol), potassium carbonate (3.08 g, 16.38 mmol), and copper powder (102 mg, 1.61 mmol). After heating at 130° C. overnight, the reaction mixture was cooled to room temperature and poured to ice—1 N HCl solution (300 mL) slowly. The solution was stirred until the brown solid was formed. The solid was filtered off and washed with cold water to yield a brown solid (3.1 g). A crude solid was dissolved in conc. sulfuric acid (20 mL) and heated at 80° C. for 1 hour. After cooling to room temperature, the reaction mixture was poured to ice (350 mL volume) and stirred for 1 hour. The precipitated solid was filtered off and re-suspended in 2.5% aq. sodium carbonate solution. The solid was filtered and washed with cold water and dried under vacuum. The solid was further recrystallized in pyridine or pyridine/water to yield 1.23 g of S3 (Y=O) (60%, two steps) as a yellowish-brown solid. $^1$H-NMR (DMSO-d6) δ 8.37 (d, J=2.0, 1H), 8.32 (d, J=8.4, 1H), 8.15 (dd, J=2.0, 8.4, 1H), 7.88 (d, J=8.8, 1H), 6.75 (bs, 2H), 6.72 (dd, J=2.0, 8.8, 1H), 6.56 (d, J=2.0, 1H). ESI-MS m/z (H+H) calc'd: 257.2. found 257.1.

Example 2

Synthesis of 3-Amino-6-nitro-10H-acridin-9-one (S3, Y=NH)

The compound S3 (Y=NH) was prepared using 2-chloro-4-nitrobenzoic acid and 3'-aminoacetanilide in the same way as S3 (Y=O). $^1$H-NMR (DMSO-d6) δ 11.54 (s, 1H), 8.32 (d, J=8.8, 1H), 8.26 (d, J=2.0, 1H), 7.92 (d, J=8.8, 1H), 7.86 (d, J=2.0, 8.4, 1H), 6.60 (dd, J=2.0, 8.8, 1H), 6.43 (d, J=2.0, 1H), 6.36 (bs, 2H). ESI-MS m/z (M+H) calc'd: 256.1. found 256.1.

Example 3

Synthesis of 3-Amino-6-nitro-thioxanthen-9-one (S3, Y=S)

3'-acetamidothiophenol (S2, Y=S) was prepared from 3'-aminothiophenol and acidic anhydride in ethyl acetate. To a solution of 3'-aminothiophenol (1.0 mL, 9.42 mmol) in ethyl acetate (50 mL) was added acidic anhydride (10.40 mmol) at 0° C., and slowly warmed up to room temperature while stirring for 1 hr. The reaction mixture was diluted with ethyl acetate and washed with 1N HCl and brine solution. The organic layer was dried over sodium sulfate, and the filtrate was concentrated and purified by silica column chromatography (ethyl acetate/hexane=1/1) (1.34 g, 85%), which was used for preparation of S3 (Y=S) in the same way as S3 (Y=O). The resulting solid S3 (Y=S) was purified by silica gel column chromatography (ethanol/methylene chloride) to give a brownish solid (25%). $^1$H-NMR (CDCl$_3$+CD$_3$OD) δ 8.69 (d, J=8.8, 1H), 8.45 (d, J=2.4, 1H), 8.34 (d, J=8.8, 1H), 8.19 (dd, J=2.4, 8.8, 1H), 6.84 (dd, J=2.4, 8.8, 1H), 6.72 (d, J=2.0, 1H). ESI-MS m/z (M+H) calc'd: 273.0. found 273.2.

Example 4

Synthesis of A (3-Amino-6-amino-xanthen-9-one)

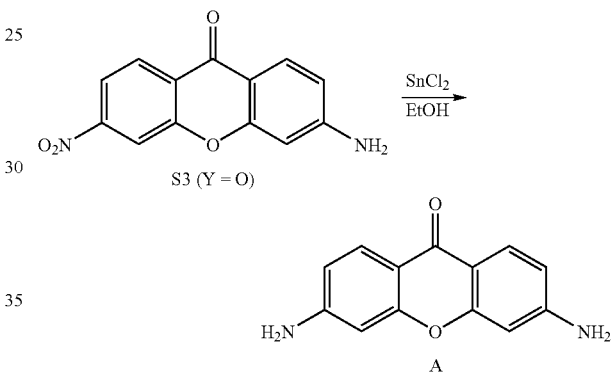

To a solution of S3 (540 mg, 2.11 mmol) dissolved in ethanol (50 mL) tin chloride dihydrate was added (1.90 g, 8.44 mmol) and refluxed overnight. After completed, the reaction mixture was concentrated and solidified by adding aq. 1N-NaOH solution. The solid was filtered and washed with water, and recrystallized from aqueous pyridine to give the compound A (219 mg, 45.8%). $^1$H-NMR (CDCl$_3$+CD$_3$OD) δ 7.98 (d, J=8.8, 2H), 6.65 (dd, J=2.4, 8.8, 2H), 6.60 (d, J=2.4, 2H). ESI-MS m/z (M+H) calc'd: 227.1. found 227.2$^+$.

Example 5

Synthesis of B (3-Amino-6-dimethylamino-xanthen-9-one)

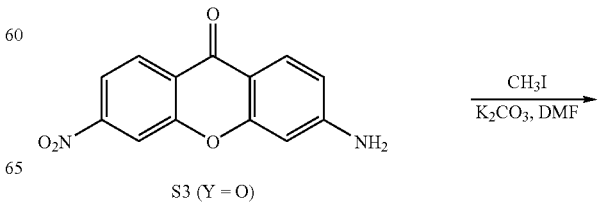

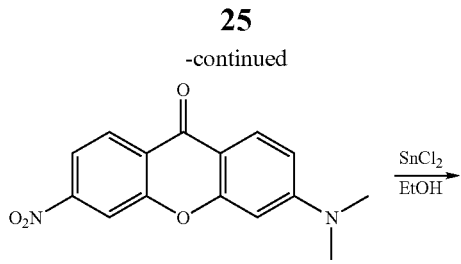

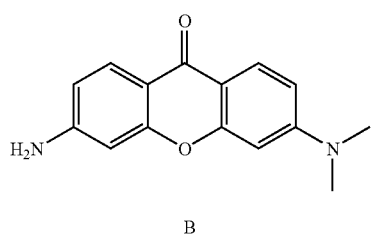

B

To a solution of S3 (1.2 g, 4.68 mmol) in DMF (40 mL) was added potassium carbonate (1.6 g, 11.57 mmol) and iodomethane (1.7 mL, 27.3 mmol). After heating at 100° C. for 2 days, the mixture was cooled to room temperature, and diluted with dichloromethane and washed with aq. 1N HCl, aq. NaHCO$_3$ and brine solution. The organic layer was dried over sodium sulfate, and the filtrate was concentrated and solidified in EA/Hexane (660 mg). To a crude compound in ethanol (50 mL) was added tin chloride dihydrate (2.09 g, 9.27 mmol). After refluxing overnight, the solution was concentrated completely and solidified in aq. 1N NaOH solution. The solid was filtered and washed with water, and purified by silica gel column chromatography to give an orange solid (400 mg, 33.6%, two steps). $^1$H-NHR (CDCl$_3$) δ 8.13 (d, J=8.8, 1H), 8.10 (d, J=8.8, 1H), 6.70 (dd, J=2.4, 8.8, 1H), 6.61 (dd, J=2.0, 8.4, 1H), 6.53 (d, J=2.4, 1H), 6.47 (d, J=2.8, 1H), 4.20 (bs, 2H), 3.10 (s, 6H). ESI-MS m/z (M+H) calc'd: 255.1. found 255.2$^+$.

Example 6

Synthesis of C
(3-Amino-6-piperidin-1-yl-xanthen-9-one)

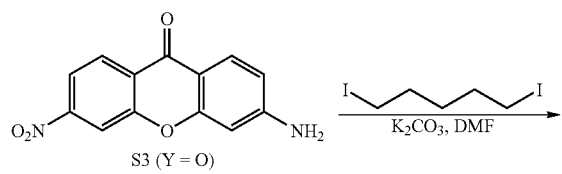

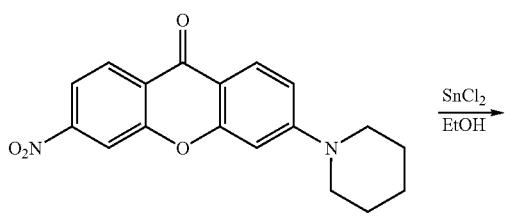

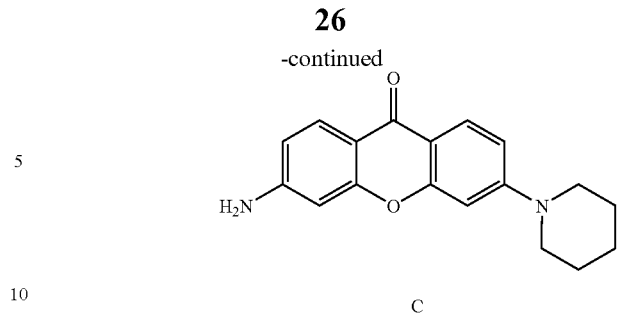

C

To a solution of S3 (1.08 g, 4.22 mmol) in DMF (40 mL) was added potassium carbonate and 1,5-diiodopentane (3.2 mL, 21.5 mmol). After heating at 100° C. until completed, the reaction mixture was cooled to room temperature and diluted with dichloromethane, and washed with aq. 1N HCl, aq. NaHCO$_3$, and brine solution. The organic layer was dried over sodium sulfate, and the filtrate was concentrated and purified by silica gel column chromatography (methanol/MC=1:80) to give a deep orange solid (620 mg). To the solid in ethanol (50 mL) tin chloride dihydrate (1.28 g, 5.67 mmol) was added and refluxed overnight. After completion, the reaction mixture was concentrated and purified by silica gel column chromatography (ethanol/MC=1:50) to give a product C (200 mg, 16.2%, two steps). $^1$H-NHR (CDCl3) δ 8.03 (d, J=8.8, 1H), 7.98 (d, J=8.4, 1H), 6.87 (dd, J=2.0, 8.8, 1H), 6.65 (d, J=2.4, 1H), 6.63 (dd, J=2.0, 8.8, 1H), 6.53 (d, J=2.0, 1H), 4.33 (s, 2H), 3.37 (bs, 4H), 1.68 (bs, 6H). ESI-MS m/z (M+H) calc'd: 295.1. found 295.0$^+$.

Example 7

Synthesis of Compound D
(3-Amino-6-hydroxy-xanthen-9-one)

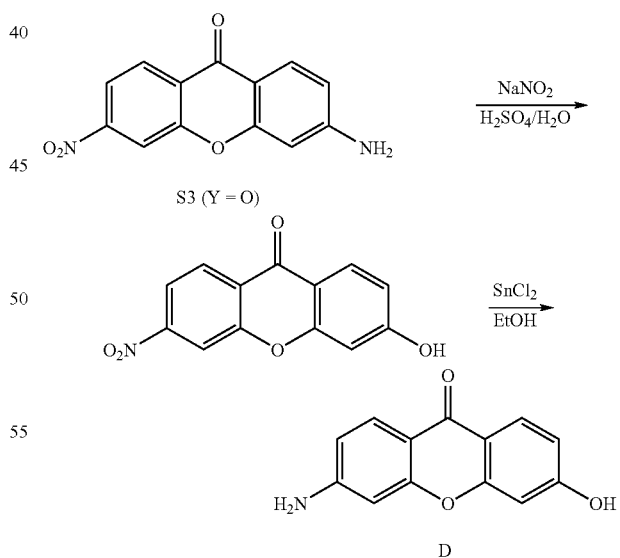

D

To a solution of S3 (600 mg, 2.34 mmol) in concentrated sulfuric acid and water (5 mL/5 mL) was added dropwise a solution of sodium nitrite (480 mg, 6.96 mmol) in water (1 mL) at 0° C. The reaction mixture was slowly warmed to room temperature while stirring for 1.5 hr and poured into boiling water (20 mL). After stirring at 95° C. for 30 min, the solution was cooled to room temperature. The precipitate was filtered and washed with cold water to yield the solid. A crude solid was refluxed overnight with tin chloride dihydrate (2.11 g, 9.36 mmol) in ethanol (50 mL). The reaction mixture was concentrated and solidified by adding aq. NaHCO$_3$ solution. The solid was filtered and washed with cold water, and purified by silica gel column chromatography to yield D (160 mg, 30%, two steps) as a yellow solid. $^1$H-NMR (CDCl$_3$+CD$_3$OD) δ 8.08 (d, J=8.8, 1H), 7.99 (d, J=8.4, 1H), 6.84 (dd, J=2.4, 8.8, 1H), 6.80 (d, J=2.0, 1H), 6.68 (dd, J=2.4, 8.8, 1H), 6.58 (d, J=2.0, 1H). ESI-MS m/z (M+H) calc'd: 228.1. found 228.0$^+$.

Example 8

Synthesis of 3-Amino-6-dimethylamino-10-methyl-10H-acridin-9-one (E)

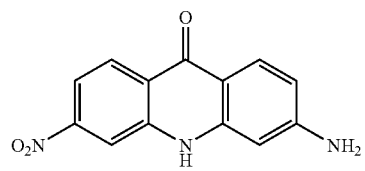

S3 (Y = NH)

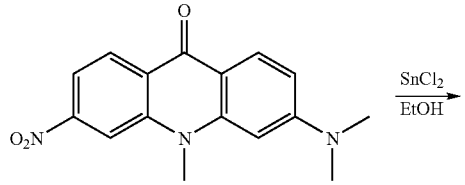

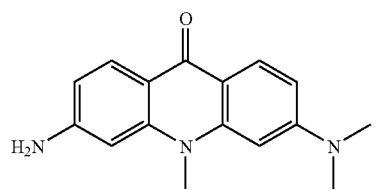

E

To a solution of S3 (2.0 g, 7.55 mmol) in DMF/THF (6.6 mL/80 mL) was added sodium hydride (906 mg, 37.7 mmol) at 0° C. After stirring for 10 min, iodomethane (1.88 mL, 30.2 mmol) was added and stirred overnight. Ethyl acetate was added to the reaction mixture, and the resulting precipitate was filtered. The solid was purified by silica gel column chromatography (methanol/MC=1:50) to give a brown solid (450 mg). To a solid in ethanol (50 mL) tin chloride dihydrate (1.38 g, 6.14 mmol) was added and refluxed overnight. After completion, the reaction mixture was concentrated and solidified by adding 1N aq. NaOH solution. The solid was filtered and washed with water, and purified by column chromatography, yielding E (400 mg, 20.0%, two steps). $^1$H-NMR (CDCl$_3$+CD$_3$OD) δ 8.27 (d, J=9.2, 1H), 8.21 (d, J=8.4, 1H), 6.78 (dd, J=2.4, 9.2, 1H), 6.69 (d, J=2.0, 1H), 6.66 (dd, J=1.6, 8.4, 1H), 6.44 (d, J=2.0, 1H), 3.81 (s, 3H), 3.18 (s, 6H). ESI-MS m/z (M+H) calc'd: 268.1. found 268.2$^+$.

Example 9

Synthesis of 3-Amino-6-ethylamino-xanthen-9-one (F)

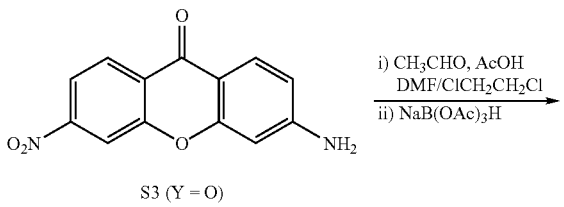

S3 (Y = O)

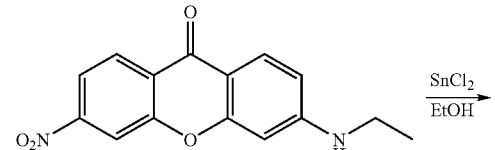

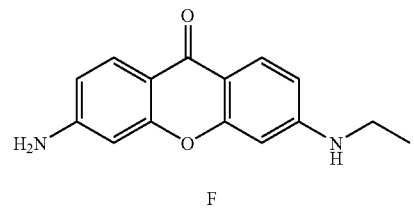

F

To a solution of S3 (1.0 g, 3.90 mmol) in DMF (5 mL) and 1,2-dichloroethane (20 mL) were added acetaldehyde (0.438 mL, 7.80 mmol) and acetic acid (1.4 mL). After stirring for 1 hr, sodium triacetoxyborohydride (2.48 g, 11.7 mmol) was added and stirred overnight. The reaction mixture was diluted with dichloromethane and then washed with aq. NaHCO$_3$ and brine solution. The organic layer was dried over sodium sulfate and concentrated, and column chromatographed on silica gel (ethanol/dichloromethane=1/100) to yield a deep orange solid (667 mg, 60%). $^1$H-NMR (DMSO-d6) δ 8.34 (d, J=2.4, 1H), 8.32 (d, J=8.8, 1H), 8.16 (dd, J=2.0, 8.8, 1H), 7.89 (d, J=8.8, 1H), 7.28 (broad t, J=5.2, 1H), 6.76 (dd, J=2.0, 8.8, 1H), 6.51 (d, J=2.0, 1H), 3.22 (m, 2H), 1.22 (t, J=7.2, 3H). ESI-MS m/z (M+H) calc'd: 285.1. found 285.0 The solid (660 mg) was refluxed overnight with tin chloride dihydrate (2.11 g, 9.35 mmol) in ethanol (80 mL). The reaction mixture was concentrated and solidified by adding aq. NaOH solution. The filtered solid was purified by silica gel column chromatography (ethanol/dichloromethane) to give compound F as a yellow solid (243 mg, 41%). $^1$H-NMR (CDCl$_3$) δ 8.09 (d, J=8.8, 1H), 8.06 (d, J=8.8, 1H), 6.61 (dd, J=2.0, 8.4, 1H), 6.53 (d, J=2.0, 1H), 6.53 (dd, J=2.4, 8.8, 1H), 6.40 (d, J=2.4, 1H), 4.22 (bs, 1H), 4.19 (bs, 2H), 3.27 (m, 2H), 1.32 (t, J=7.2, 3H). ESI-MS m/z (M+H) calc'd: 255.1. found 255.2$^+$.

Example 10

Synthesis of 3,6-Diamino-thioxanthen-9-one (G)

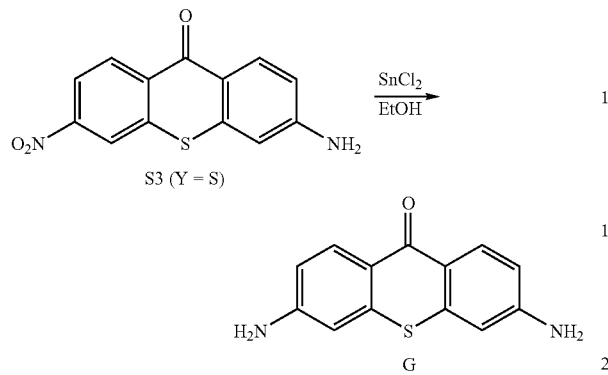

To a solution of S3 (900 mg, 3.31 mmol) in ethanol (125 mL) was added tin chloride (4 g, 17.7 mmol), followed by overnight refluxing. The reaction mixture was concentrated and solidified in aq. 1N NaOH solution. The solid was filtered, dried, and column chromatographed on silica gel (ethanol/dichloromethane), yielding G (250 mg, 32%) as a yellow solid. $^1$H-NMR (CDCl$_3$) δ 8.40 (d, J=8.8, 2H), 6.71 (dd, J=2.0, 8.8, 2H), 6.65 (d, J=2.0, 2H), 4.12 (bs, 4H). ESI-MS m/z (M+H) calc'd: 243.1. found 243.2.

Example 11

Synthesis of H

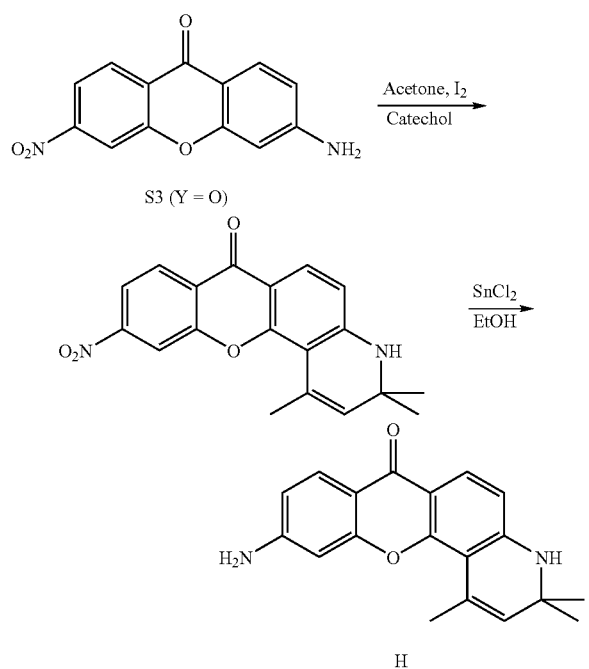

To a solution of S3 (1.2 g, 4.68 mmol) in acetone (150 mL) was added iodine (500 mg, 3.93 mmol) and catechol (600 mg, 5.45 mmol). After refluxing for 2 days, all the solvents were evaporated and the reaction mixture was solidified in methanol and aq. NaHCO$_3$ solution. The solid was filtered and washed with water. The solid was further purified by silica gel column chromatography (ethanol/dichloromethane) giving a solid (800 mg). To the crude solid in ethanol (80 mL) was added tin chloride dihydrate (2.1 g, 2.33 mmol) and refluxed overnight. The reaction mixture was concentrated and solidified in aq. 1N NaOH solution. The filtered solid was purified on silica gel chromatography (ethyl acetate/hexane), yielding H as a solid (260 mg, 18.2%, two steps). $^1$H-NMR (CDCl3) δ 8.07 (d, J=8.4, 1H), 7.98 (d, J=8.4, 1H), 6.61 (dd, J=2.0, 8.4, 1H), 6.53 (d, J=2.4, 1H), 6.44 (d, J=8.8, 1H), 5.29 (s, 1H), 4.34 (bs, 1H), 4.29 (bs, 2H), 2.42 (d, J=1.2, 3H), 1.32 (s, 6H). ESI-MS m/z (M+H) calc'd: 307.1. found 307.2$^+$.

Example 12

Synthesis of 3-Amino-6-dibutylamino-xanthen-9-one (I)

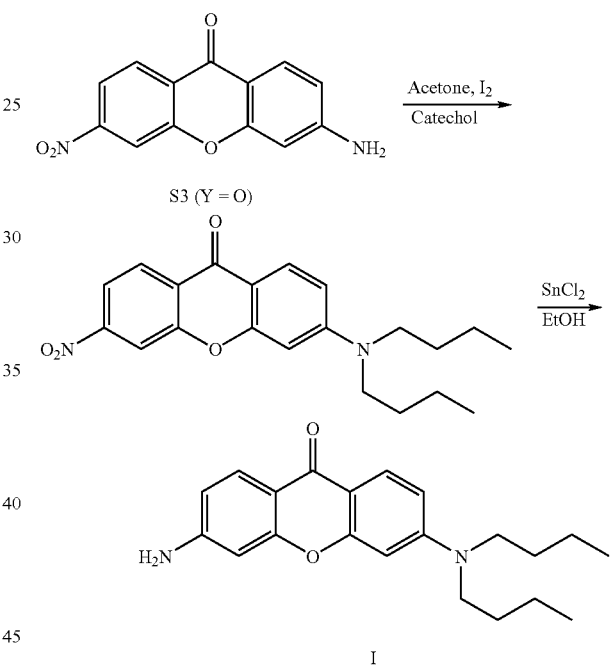

To a solution of S3 (500 mg, 1.95 mmol) in THF and DMF (30 mL/10 mL) was added sodium hydride (1 g, 39.6 mmol) and iodobutane (1.8 mL, 15.8 mmol) at 0° C. The solution was then warmed slowly to room temperature and stirred overnight. The solution was diluted with dichloromethane and washed with 1N HCl solution, aq. NaHCO$_3$ solution and brine. The organic layer was dried over sodium sulfate. The filtrate was concentrated and purified by silica gel column chromatography (ethyl acetate/hexane=1/10) to yield the orange solid (250 mg). The solid was refluxed overnight with tin chloride dihydrate (450 mg, 2.0 mmol) in ethanol (50 mL). The reaction mixture was concentrated and solidified in aq. 1N NaOH solution. The filtered solid was purified by silica gel column chromatography (ethyl acetate/hexane=1/2), yielding I as a yellow solid (150 mg, 22.8%). $^1$H-NMR (CDCl$_3$) δ 8.09 (d, J=1.6, 1H), 8.07 (d, J=2.0, 1H), 6.63 (dd, J=2.4, 8.8, 1H), 6.58 (dd, J=2.4, 8.8, 1H), 6.53 (d, J=2.4, 1H), 6.40 (d, J=2.4, 1H), 4.18 (bs, 2H), 3.36 (t, J=7.8, 4H), 1.63 (m, 4H), 1.40 (sextet, J=7.4, 4H), 0.99 (t, J=7.4, 6H). ESI-MS m/z (M+H) calc'd: 339.2. found 339.2$^+$.

Example 13

Synthesis of J

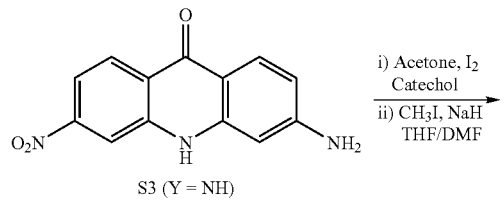

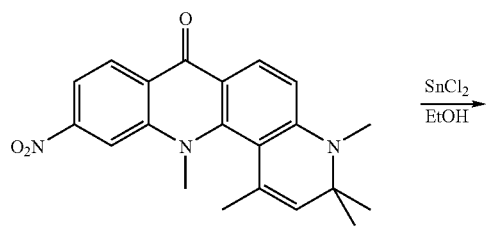

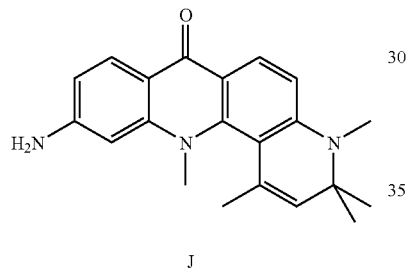

The solution of S3 (3 g, 11.76 mmol), iodine (600 mg, 4.72 mmol), and catechol (600 mg, 5.45 mmol) in acetone (200 mL) was refluxed for 2 days. All the solvents were evaporated, and the reaction mixture was solidified in methanol (40 mL) and aq. NaHCO$_3$ (400 mL). The solid was filtered and washed with water and dried under vacuum. The solid (2.0 g) was dissolved in THF (120 mL) and DMF (20 mL). The sodium hydride (1.15 g, 47.7 mmol) was added at 0° C. After stirring for 10 min, iodomethane (1.86 mL, 29.8 mmol) was added and stirred overnight at room temperature. The reaction mixture was diluted with ethyl acetate and washed with aq. NH$_4$Cl solution, aq. NaHCO$_3$, and brine. The organic layer was dried over sodium sulfate. The filtrate was concentrated and purified by silica gel column chromatography, giving a brown solid (500 mg). The solid was refluxed overnight with tin chloride dihydrate (450 mg, 2.0 mmol) in ethanol (50 mL). The reaction mixture was concentrated and solidified in aq. 1N NaOH solution. The filtered solid was further purified by silica gel column chromatography (ethanol/dichloromethane), yielding J (351 mg, 9.0%, three steps) as a yellow solid. $^1$H-NMR (CDCl$_3$) δ 8.28 (d, J=8.4, 1H), 8.24 (d, J=9.2, 1H), 6.70 (d, J=8.8, 1H), 6.59 (dd, J=2.0, 8.8, 1H), 6.54 (d, J=2.0, 1H), 5.28 (d, J=1.2, 1H), 4.18 (bs, 2H), 3.67 (s, 3H), 3.04 (s, 3H), 1.97 (d, J=1.2, 3H), 1.57 (s, 3H), 1.10 (s, 3H). ESI-MS m/z (M+H) calc'd: 334.2. found 334.1$^+$.

Example 14

Synthesis of 3-Amino-6-diethylamino-10H-acridin-9-one (K)

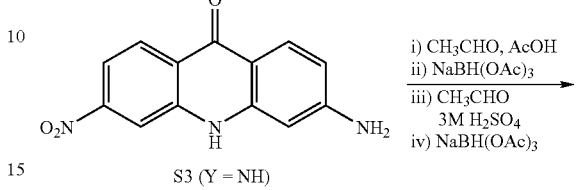

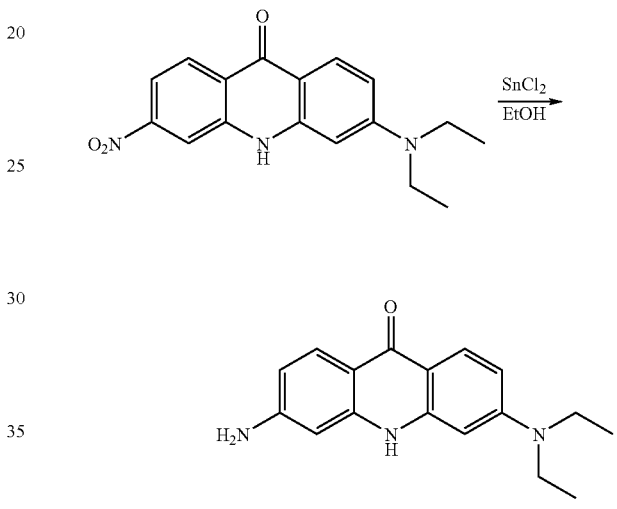

To a solution of S3 (2.7 g, 10.5 mmol) in DMF (15 mL) and 1,2-dichloroethane (40 mL), acetaldehyde (1.78 mL, 31.0 mmol) and acetic acid (3.63 mL, 63.0 mmol) were added. After stirring at room temperature for 1 hr, sodium triacetoxyborohydride (3.35 g, 15.8 mmol) was added and stirred overnight. The reaction mixture was diluted with dichloromethane and washed with aq. NaHCO$_3$, and brine. The combined organic layers were dried over sodium sulfate. The filtrate was concentrated and solidified in methanol. The filtered solid was dried under vacuum. The solid was dissolved in THF (100 mL), and added acetaldehyde (1.6 mL) and 3.5 M sulfuric acid (12.11 mL). After stirring for 1 hr, sodium triacetoxyborohydride (1.8 g) was added and stirred overnight. The reaction mixture was concentrated and basified with aq. 1N NaOH solution (pH 9-10). The resulting solid was filtered and dried under vacuum. The solid was reduced with tin chloride dihydrate, yielding K (300 mg, 10.1%, three steps) as a yellow solid. $^1$H-NMR (CDCl$_3$+CD$_3$OD) δ 8.14 (d, J=9.2, 1H), 8.10 (d, J=8.8, 1H), 6.68 (dd, J=2.4, 9.2, 1H), 6.58 (dd, J=2.0, 8.8, 1H), 6.44 (d, J=2.4, 1H), 6.36 (d, J=2.4, 1H), 3.48 (q, J=7.2, 4H), 1.25 (t, J=7.2, 6H). ESI-MS m/z (M+H) calc'd: 282.2. found 282.1.

Example 15

Synthesis of L (3-Amino-6-[(3-dimethylamino-propyl)-ethyl-amino]-xanthen-9-one)

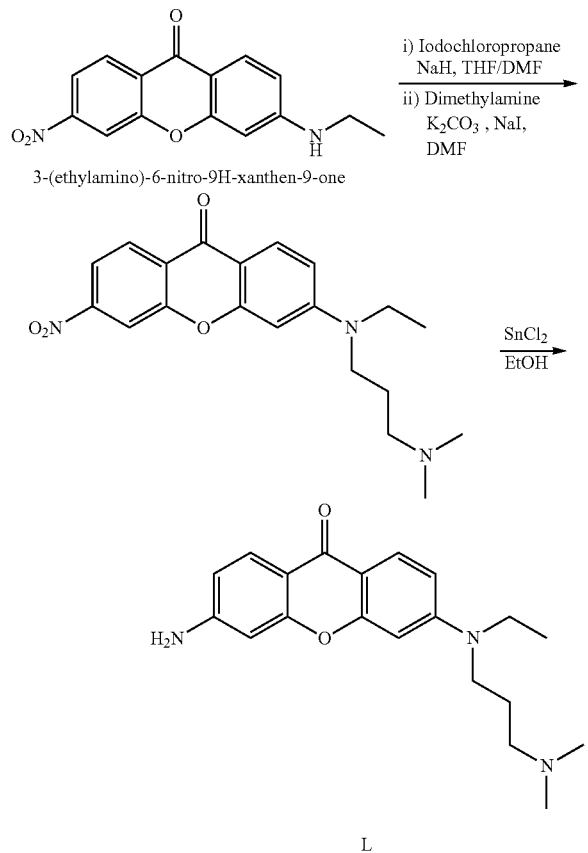

To a solution of 3-(ethylamino)-6-nitro-9H-xanthen-9-one (1.38 g, 4.86 mmol) in THF/DMF (50 mL/5 mL) was added sodium hydride (350 mg, 14.6 mmol) at 0° C. After stirring for 10 min, iodochloropropane (1.0 mL, 9.72 mmol) was added and warmed up slowly to room temperature while stirring overnight. The reaction mixture was diluted with dichloromethane and washed with 1N HCl, aq. NaHCO$_3$, and brine. The organic layer was dried over sodium sulfate, and the filtrate was concentrated and purified on silica gel column chromatography (ethyl acetate/hexane) to give the orange solid (690 mg, 39.3%). To the solid (640 mg, 1.78 mmol) in DMF (15 mL) was added potassium carbonate (490 mg, 3.56 mmol), sodium iodide (320 mg, 2.14 mmol), and dimethylamine (2 M in THF) (2.6 mL, 5.34 mmol). The reaction mixture was heated at 80° C. overnight, and all the solvents were evaporated under vacuum. The reaction mixture was dissolved in methanol and dichloromethane, the precipitating salts were removed by filtration, and the filtrate was concentrated and dried under vacuum. The crude mixture was treated with tin chloride to reduce nitro group reduction, yielding L as a yellow solid (210 mg, 34.7%, two steps). $^1$H-NMR (CD$_3$OD+CDCl$_3$) δ 8.03 (d, J=9.2, 1H), 7.96 (d, J=8.4, 1H), 6.74 (dd, J=3.4, 8.8, 1H), 6.66 (dd, J=2.0, 8.8, 1H), 6.56 (d, J=2.0, 1H), 6.53 (d, J=2.8, 1H), 3.52 (m, 4H), 2.81 (t, J=7.8, 2H), 2.59 (s, 6H), 1.99 (m, 2H), 1.26 (t, J=7.0, 3H). ESI-MS m/z (M+H) calc'd: 340.2. found 340.1.

Examples 16-19

General Procedure for Library Synthesis on Solid Support

Example 16

Preparation of 2-chlorotrityl chloride from 2-chlorotrityl alcohol resin

2-Chlorotrityl alcohol resin (500 mg 1.37 mmol/g) was suspended in dichloromethane (5 mL) for 10 min. Thionyl chloride (150 µL, 2.06 mmol) was added, and the vial was shaken for 2 hours at room temperature. The resin was filtered, washed with dichloromethane and acetonitrile, and then dried.

Example 17

General Procedure for Loading A-L to Solid Resin

Each compound (A-L, the T$^1$ building blocks in Table 1) (0.411 mmol) was dissolved in dichloromethane (5 mL) using 20 mL vial, and, if not soluble, DMF was added (1-2 mL). The solution was added to a 2-chlorotrityl chloride resin (0.274 mmol) suspended in dichloromethane (1 mL), and pyridine (4.11 mmol) was added. After stirring for 4 hrs, the resin was filtered through 3 mL cartridge and washed with DMF (×5), methanol (×10), and dichloromethane (×10), and dried.

Example 18

General Procedure of Grignard Reaction and Cleavage from the Resin

For each reaction, a resin (10 mg) was suspended in freshly distilled THF (0.1 mL) in a 4 mL glass vial, and each Grignard reagent (0.5M in THF) (1.5 mL) was added and capped tightly with a TFE lined cap, and heated at 62-64° C. on standard heat-block for 2-4 days. The resin was filtered through 1 mL cartridge and washed with dichloromethane (×5), DMF (×5), methanol (×5), and dichloromethane (×5). The resin was dried and treated with 1% TFA in dichloromethane (1.5 mL) for 15 min, and the solution was drained to the 4 mL vial, and dried using SpeedVac.

Example 19

Modified Procedure for T$^1$ Building Block (D) Series

Compound D (from the list of building blocks T$^1$ in Table 1) was loaded on the resin as described, but was preceded by butyldimethylsilyl group protection. The resin was suspended in DMF, t-butyldimethylsilyl chloride (5 eq.) and imidazole (10 eq.) and stirred overnight. The solution was drained, and the resin was washed with DMF, methanol, and dichloromethane continuously. The dried resin was reacted with Grignard reagents, and the resin was cleaved as described above.

Example 20

Structure and HPLC Traces of Representative Compounds

The representative HPLC traces and mass spectra are illustrated in FIGS. 1 to 5 to show the purity and identity of each compound. All compounds were identified by LC-MS from Agilent Technology, using a C18 column (20×4.0 mm), with 4 minutes elution using a gradient solution of $CH_3CN$—$H_2O$ (containing 0.1% acetic acid), with UV detector and an electrospray ionization source. All of HPLC traces at 250 nm showed over 95% purity when calculated on the basis of the integration.

Example 21

Characterization of the Specific Rosamine Molecule A4

Absorption was taken using SpectraMax Plus absorbance plate reader, showing a maximum wavelength at 500 nm. Fluorescence emission was taken using Spectra Max Gemini XSF, giving a maximum wavelength at 530 nm. Molecule A4 showed a strong green fluorescence upon irradiation of 365 nm UV. See FIGS. 6A-D.

Example 22

Localization of Rosamine Molecules

3T3 cells were grown on the glass bottom, 96-well black plates, and each rosamine derivative compound is added to the cell culture to reach the desired concentration (500 nM to 5 μM) and incubated for half an hour. The optical fluorescence microscope was used for investigating the localization of each compound in the cell. Many of them have shown localization to mitochondria. Several examples of different localizations are selected and shown in FIG. 7.

Example 23

Screening of Rosamine Libraries

The rosamine derivative compounds were screened toward 47 different analytes that include proteins, polysaccharides, nucleic acids, and metal ions. The stock solution of each dye (50 μL) in HEPES (20 mM, pH=7.4) or PBS (20 mM, pH=7.4) was prepared, and diluted with the each analyte (50 μL, 1.0 mg/mL or 200 μM) in the same buffer solution. The final dye concentration varied from 0.5 μM to 10 μM. The fluorescence intensity fold changes of each dye in the presence of analytes were calculated by comparing the fluorescence intensity at the maximum emission wavelength with/without the analyte. The fold changes of all the compounds were summarized in FIG. 8.

Example 24

Fluorescence Emission Response of Molecule G13

Molecule G13 was screened for fluorescence intensity change toward 13 different macromolecules that include proteins, polysaccharides, and nucleic acids (i.e. HSA, BSA, dsDNA, RNA, peroxidase, cellulase A, protease A, lipase, lysozyme, papain, heparin, hemoglobin, and hemicellulase). Molecule G13 (10 μM) exhibited a highly selective fluorescence increase (12.5 fold change) toward human serum albumin (HSA). Interestingly, a very close protein, bovine serum albumin (BSA) showed only small response (1.5 fold change) to G13, with almost no change for all other proteins. See FIG. 9.

Example 25

In vitro Fluorescence Response of H22 to Glutathione (GSH)

Figure 12:
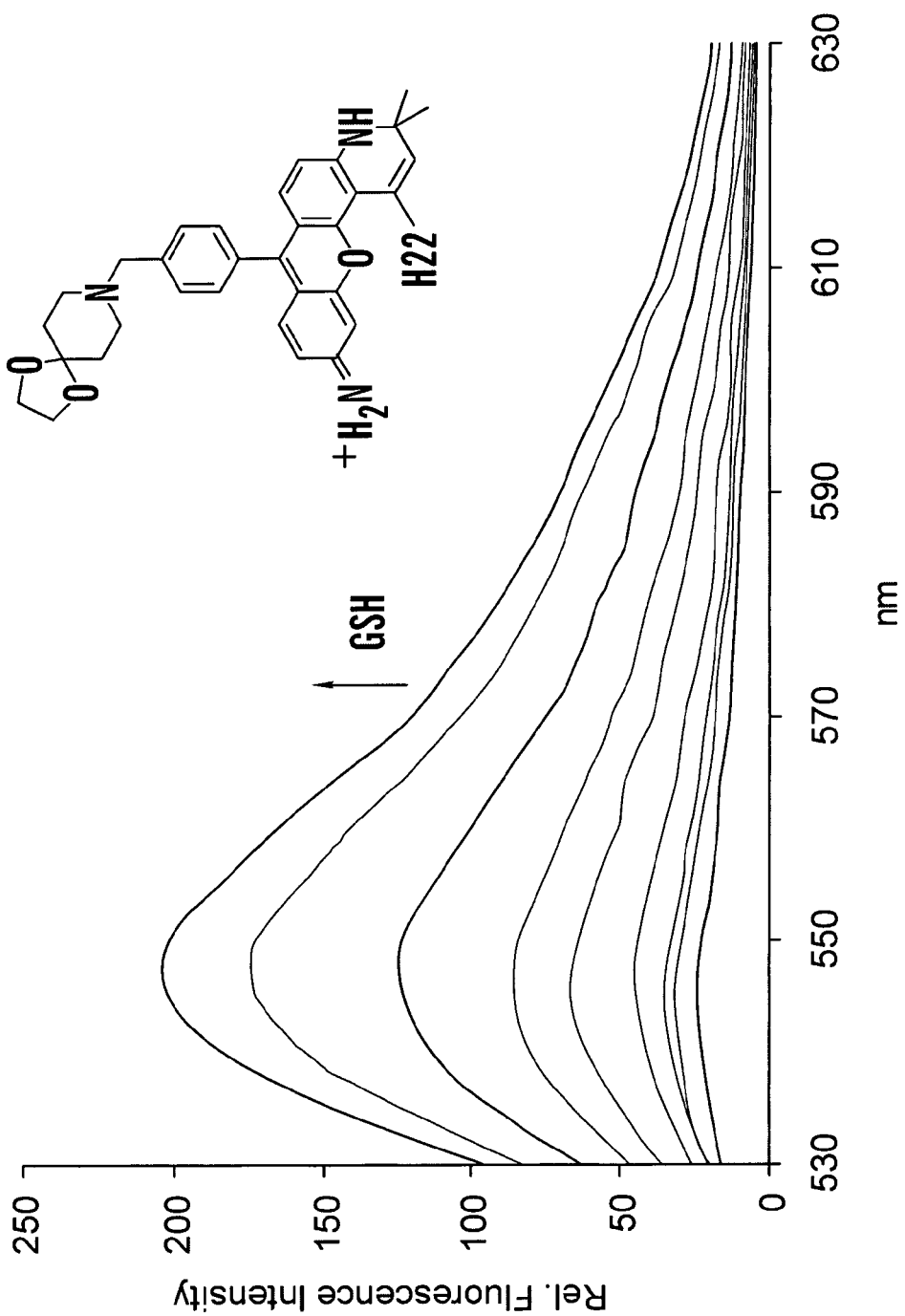
FIG. 12 shows the fluorescence responses of H22 in Table 1 (3 μM) toward GSH in 0, 0.01, 0.05, 0.1, 0.25, 0.5, 1.0, 2.5, 5 mM. H22 was incubated with GSH for 30 min in 50 mM HEPES, pH 7.4. Spectra were obtained with excitation at 500 nm.
Figure 13:
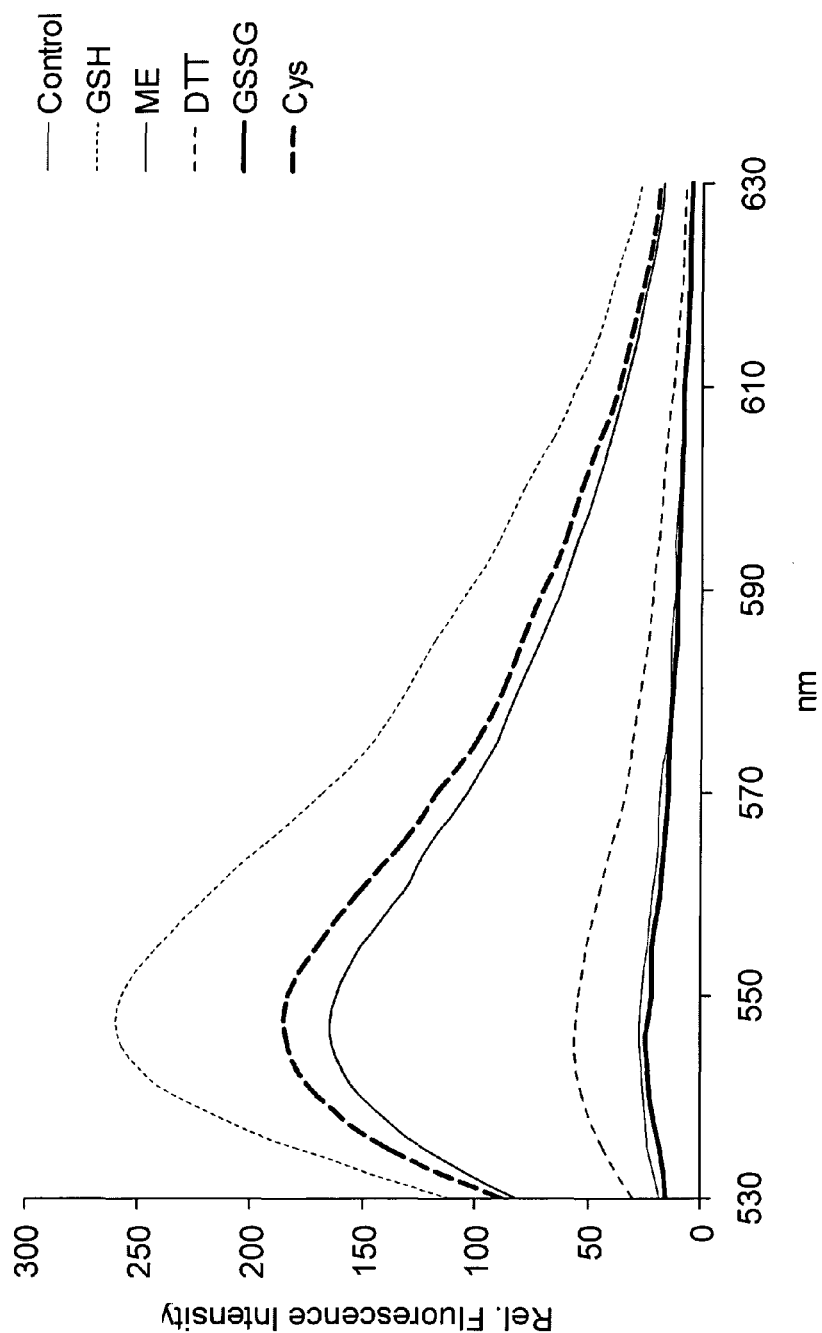
FIG. 13 shows the fluorescence responses of H22 in Table 1 (3 μM) toward GSSG and various thiols (5 mM) in 50 mM HEPES (pH 7.4) after 30 min incubation with excitation of 500 nm

Molecule H22 exhibited a highly selective response toward reduced glutathione (GSH). Under physiological conditions (pH 7.4, 50 mM HEPES), H22 (3 μM) showed a marked fluorescence increase upon addition of GSH (5 mM) by ca. 11-fold in 30 min (FIG. 12). H22 did not show any fluorescence response to GSSG (5 mM) while several thiol-containing analytes (5 mM) such as DTT, β-mercaptoethanol (ME) and cysteine showed modest responses to H22 (FIG. 13)

Example 26

Imaging in vivo Glutathione (GSH) with H22

Figure 14A:
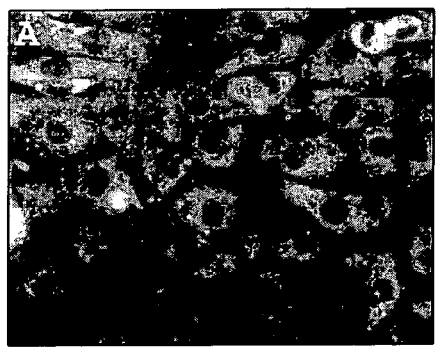
FIGS. 14A-D show the fluorescence microscopic images of live 3T3 cells stained with H22 in Table 1.
Figure 14B:
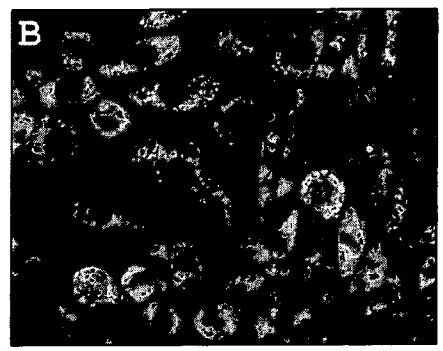
Figure 14C:
Figure 14D:
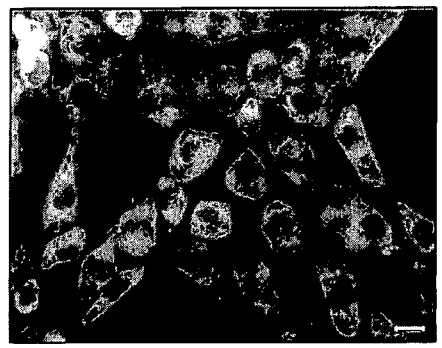

The capability of H22 to monitor GSH in a living cell was tested. α-Lipoic acid is known to enhance the reduced GSH level in a variety of cells. Thus, 3T3 cells were supplemented with α-lipoic acid (250 μM) for 48 hr. Subsequent staining of cells with H22 (3 μM) showed a clear increase in the intracellular fluorescence intensity in α-lipoic acid treated cells (FIG. 14B) compared to non-treated cells (FIG. 14A). When N-methylmaleimide (NMM, thiol reactive reagent: FIG. 14C) or diamide (thiol oxidant: FIG. 14D) was supplemented to α-lipoic acid-treated cells stained with H22, a distinct decrease of fluorescence intensity was observed.

Example 27

Monitoring the Glutathione (GSH) Depletion with H22

Figures 15A, 15B, 15C, 15D:
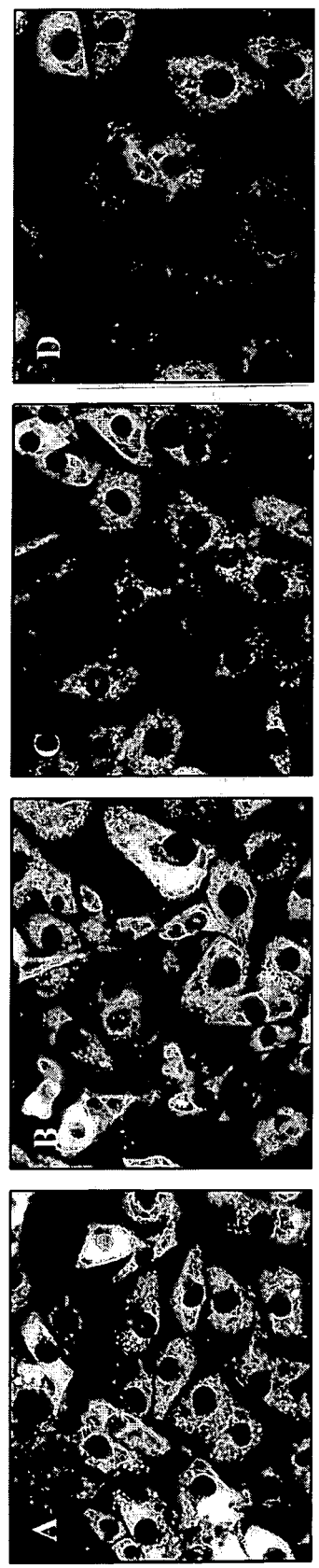
FIGS. 15A-D show the fluorescence images of 3T3 cells stained with H22 in Table 1 that monitored the GSH depletion upon treatment of BSO. 3T3 cells were stained with H22 (3 μM). Subsequently, a series of concentration of BSO was incubated for 60 min. 0 μM (FIG. 15A), 25 μM (FIG. 15B), 50 μM (FIG. 15C), 100 μM of BSO (FIG. 15D).

The GSH depletion was monitored by H22 when 3T3 cells were incubated with BSO (buthionine sulfoximine; GSH synthesis inhibitor). 3T3 cells were stained with H22 (3 μM). Subsequently, a series of concentration of BSO was incubated for 60 min, exhibiting a decrease of fluorescence intensity. See FIGS. 15A-D, which show the following BSO concentrations: 0 μM (FIG. 15A), 25 μM (FIG. 15B), 50 μM (FIG. 15C), and 100 μM (FIG. 15D).

Example 28

Fluorescence Emission Response of Molecule J and L

Figure 10A:
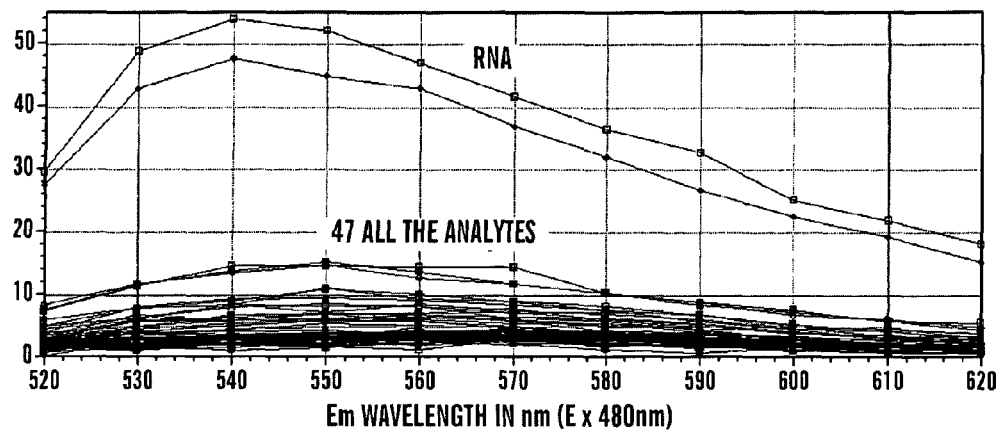
FIG. 10A shows the selective increase of fluorescence intensity of J in the presence of RNA, duplicated.
Figure 10B:
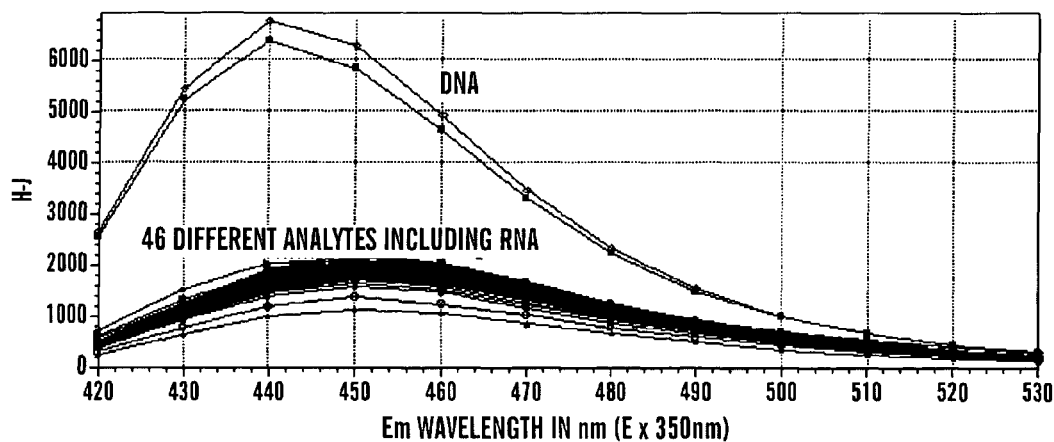
FIG. 10B shows the selective increase of fluorescence intensity of L in the presence of DNA, duplicated.

From the screening of rosamine libraries toward 47 different analytes that include proteins, polysaccharides, nucleic acids, and metal ions (FIG. 8), molecule J exhibited a selective response to RNA and molecule L showed a selective response to DNA (FIG. 10A-B).

Example 29

Absorbance, Fluorescent Wavelength, and Purity For the Library of Rosamine Derivative Compounds For the rosamine derivative compounds, all absorption data was obtained by a plate reader in PBS (10 mM). Purity data was calculated on the basis of the integration in the HPLC trace at 250 nm. Mass was calculated as ($M^+$) and found in ESI-MS m/e. Excitation ranges were from 480-545 nm and emission ranges were from 530-605 nm. See FIG. 11 Although the invention has been described in detail, for the purpose of illustration, it is understood that such detail is for that purpose and variations can be made therein by those skilled in the art without departing from the spirit and scope of the invention which is defined by the following claims.

What is claimed is:

1. A rosamine derivative compound of the formula:

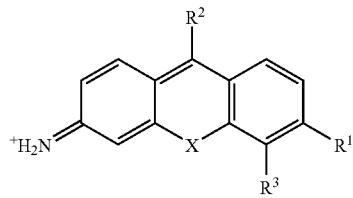

wherein:
X is O, NR$^4$, or S;
R$_1$ is NR$^4$R$^5$, OH, NR$^4$R$^6$, or

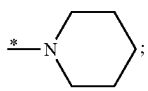

R$^2$ is substituted or unsubstituted napthyl,

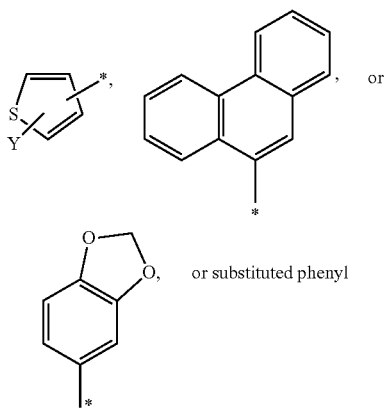

or substituted phenyl wherein the substituted form of R$^2$ has one or more substituents independently selected from the group consisting of halogen, NR$^4$R$^5$, OR$^7$, SR$^4$, aryl,

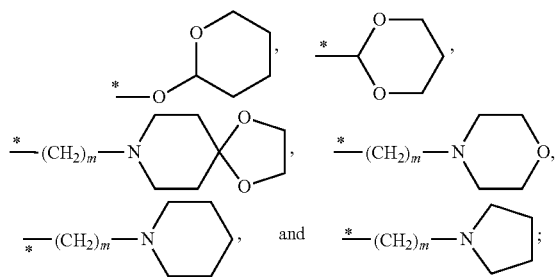

R$^3$ is H or with R$^1$ collectively forms a fused ring of the structure of

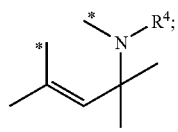

R$^4$ is H or C$_1$ to C$_6$ alkyl;
R$^5$ is H, C$_1$ to C$_6$ alkyl, or with R$^4$ collectively forms a ring structure;
R$^6$ is (CH$_2$)$_n$NR$^4$R$^8$;
R$^7$ is H, C$_1$ to C$_6$ alkyl, or aryl;
R$^8$ is H or C$_1$ to C$_6$ alkyl;
Y is alkyl or halogen;
n is 1 to 3;
m is 0 to 3; and
* is a site on a substituent which binds to the rosamine derivative compound.

2. The rosamine derivative compound of claim 1, wherein X is O.

3. The rosamine derivative compound of claim 1, wherein X is NR$^4$.

4. The rosamine derivative compound of claim 1, wherein X is S.

5. The rosamine derivative compound of claim 1, wherein R$^1$ is NR$^4$R$^5$.

6. The rosamine derivative compound of claim 1, wherein R$^1$ is OH.

7. The rosamine derivative compound of claim 1, wherein R$^1$ is NR$^4$R$^6$.

8. The rosamine derivative compound of claim 1, wherein R$^1$ is

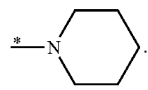

9. A method of detecting the presence, if any, of a target molecule in a sample, said method comprising:
providing a sample potentially containing a target molecule;
providing the rosamine derivative compound of claim 1, wherein said rosamine derivative compound has a first fluorescent characteristic when bound to the target molecule and a second fluorescent characteristic in an unbound state;
contacting the rosamine derivative compound with the sample under conditions effective to permit binding of any target molecule present in the sample to the rosamine derivative compound; and
detecting the presence of the target molecule in the sample as a function of the fluorescence characteristic of the rosamine derivative compound, wherein the presence of the target molecule is indicated by detection of the first fluorescent characteristic while the absence of the target molecule is indicated by detection of the second fluorescence characteristic.

10. The method of claim 9, wherein X is O.
11. The method of claim 9, wherein X is NR$^4$.
12. The method of claim 9, wherein R$^1$ is NR$^4$R$^5$.
13. The method of claim 9, wherein R$^1$ is OH.
14. The method of claim 9, wherein R$^1$ is NR$^4$R$^6$.
15. The method of claim 9, wherein the target molecule is a nucleic acid, a protein sequence, or a component of a cell.

16. A method of imaging cells comprising:
providing cells to be imaged;
providing the rosamine derivative compound of claim 1;
contacting the rosamine derivative compound with the cells to be imaged under conditions effective to permit binding of the rosamine derivative compound to the cells; and
exposing the cells to activating radiation, whereby any of the rosamine derivative compound bound to the cells fluoresces, thereby producing an image of the cells based on their fluorescent emission.

17. The method of claim 16, wherein X is O.
18. The method of claim 16, wherein X is $NR^4$.
19. The method of claim 16, wherein $R^1$ is $NR^4R^5$.
20. The method of claim 16, wherein $R^1$ is OH.
21. The method of claim 16, wherein $R^1$ is $NR^4R^6$.
22. The method of claim 16, wherein the method is carried out in vitro.
23. The method of claim 16, wherein the method is carried out in vivo.
24. The method of claim 16, wherein a tissue or an organ is imaged.
25. A rosamine derivative compound of the formula:

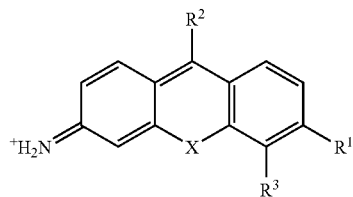

wherein:
X is O, $NR^4$, or S;
$R_1$ is $NR^4R^5$, OH, $NR^4R^6$, or

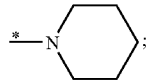

$R^2$ is substituted or unsubstituted napthyl,

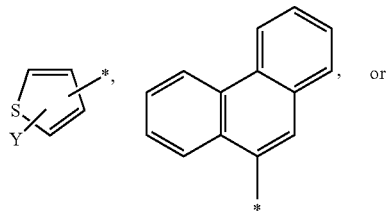

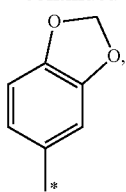

wherein the substituted form of $R^2$ has one or more substituents independently selected from the group consisting of halogen, $NR^4R^5$, $OR^7$, $SR^4$, aryl, $C_1$ to $C_6$ alkyl,

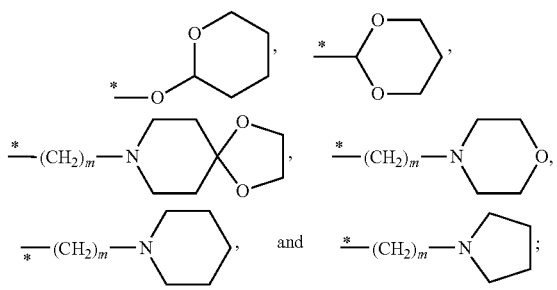

$R^3$ is H or with $R^1$ collectively forms a fused ring of the structure of

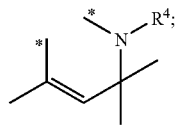

$R^4$ is H or $C_1$ to $C_6$ alkyl;
$R^5$ is H, $C_1$ to $C_6$ alkyl, or with $R^4$ collectively forms a ring structure;
$R^6$ is $(CH_2)_n NR^4R^8$;
$R^7$ is H, $C_1$ to $C_6$ alkyl, or aryl;
$R^8$ is H or $C_1$ to $C_6$ alkyl;
Y is alkyl or halogen;
n is 1 to 3;
m is 0 to 3; and
* is a site on a substituent which binds to the rosamine derivative compound.

* * * * *

UNITED STATES PATENT AND TRADEMARK OFFICE
CERTIFICATE OF CORRECTION

PATENT NO. : 8,026,110 B2
APPLICATION NO. : 11/853594
DATED : September 27, 2011
INVENTOR(S) : Young-Tae Chang and Young-Hoon Ahn It is certified that error appears in the above-identified patent and that said Letters Patent is hereby corrected as shown below:

In the Specification

Column 1, after Line 6, please insert --This invention was made with government support under GM072029 awarded by National Institutes of Health. The government has certain rights in the invention.--

Signed and Sealed this
Twentieth Day of August, 2019

Andrei Iancu
*Director of the United States Patent and Trademark Office*